(12) United States Patent
Gibson et al.

(10) Patent No.: US 7,393,637 B2
(45) Date of Patent: Jul. 1, 2008

(54) METHODS FOR DETECTING CANCER AND MONITORING CANCER PROGRESSION

(75) Inventors: Spencer B. Gibson, Winnipeg (CA); David D. Eisenstat, Winnipeg (CA)

(73) Assignee: University of Manitoba, Winnipeg, Manitoba (CA)

( * ) Notice: Subject to any disclaimer, the term of this patent is extended or adjusted under 35 U.S.C. 154(b) by 0 days.

(21) Appl. No.: 10/559,232

(22) PCT Filed: Jun. 14, 2004

(86) PCT No.: PCT/CA2004/000860

§ 371 (c)(1),
(2), (4) Date: Apr. 27, 2006

(87) PCT Pub. No.: WO2004/111641

PCT Pub. Date: Dec. 23, 2004

(65) Prior Publication Data

US 2006/0281089 A1    Dec. 14, 2006

Related U.S. Application Data

(60) Provisional application No. 60/477,777, filed on Jun. 12, 2003.

(51) Int. Cl.
*C12Q 1/68*    (2006.01)
*G01N 33/53*    (2006.01)

(52) U.S. Cl. ............................................. 435/6; 435/7.1

(58) Field of Classification Search ....................... None
See application file for complete search history.

(56) References Cited

FOREIGN PATENT DOCUMENTS

WO    WO 00/55174    9/2000
WO    WO 02/46465 A2 *    6/2002

OTHER PUBLICATIONS

Lee, H., and Paik, S. Regulation of BNIP3 in normal and cancer cells. 2006. Molecules and Cells, vol. 21 No. 1, pp. 1-6.*

Zhou, J., Schmid, T., Schnitzer, S., and Brune, B. Tumor hypoxia and cancer prevention. 2006. Cancer Letters, vol. 237, pp. 10-21.*

Burton, T.R., Henson, E.S., Baijal, P., Eisenstat, D.D., and Gibson, S.B. The pro-cell death BCL-2 family member BNIP3, is localized to the nucleus of human glial cells: implications for glioblastoma multiforme tumor cell survival under hypoxia. 2006, International Journal of Cancer, vol. 118, pp. 1660-1669.*

Reiger, R., Michaelis, A, and Green, M.M. Glossary of genetics and cytogenetics. 1976. Springer-Verlag, pp. 17-18.*

K. Guo et al, "Hypoxia induces the expressions of the pro-apoptotic gene BNIP3", Cell Death and Differentiation, 2001, vol. 8, pp. 367-376.

Cizeau Jeannick et al, "The *C. elegans* orthologue ceBNIP3 interacts with CED-9 and CED-3 but kills through a BH3- and caspase-independent mechanism", Oncogene, Nov. 16, 2000, vol. 19, No. 48, pp. 5453-5463.

Chen Gao et al, "Nix and Nip3 form a subfamily of pro-apoptotic mitochondrial proteins", Journal of Biological Chemistry, Jan. 1, 1999, vol. 274, No. 1, pp. 7-10.

C. Vande Velde et al, "BNIP3 and genetic control of necrosis-like cell death through the mitochondrial permeability transition pore", Molecular and Cellular Biology, Aug. 2000, vol. 20, No. 15, pp. 5454-5468.

S. Kothari et al, "BNIP3 plays a role in hypoxic cell death in human epithelial cells that is inhibited by growth factors EGF and IGF", Oncogene, Jul. 24, 2003, vol. 22, No. 30, pp. 4734-4744.

Eisenstat, Dr. David; NBTF Progress Report—"Oligo Fund"; Nov. 15, 2005, NBTF website, www.braintumor.org/research/past_recipients/2004_reports/Eisenstat_Oligo_detail.pdf.

* cited by examiner

*Primary Examiner*—Larry R. Helms
*Assistant Examiner*—Anne M Gussow
(74) *Attorney, Agent, or Firm*—Bereskin & Parr; Micheline Gravelle

(57) ABSTRACT

Mutant BNIP3 plays a functionally important role in the development of solid tumors and in resistance to chemotherapy and radiation treatments. The invention relates to methods of detecting cancer, methods of monitoring the progression of cancer, methods of identifying patients with cancer that is resistant to chemotherapy or radiation treatments, and diagnostic kits for performing the methods of the invention.

18 Claims, 13 Drawing Sheets

A)

B)

i)

C)

i)

D) i) wt BNIP3

E) i)

ii)

Wt BNIP3 iii)

| | |
|---|---|
| Wt BNIP3 | atgtcgcag aacggagcgc ccgggatgca ggaggagagc ctgcagggct cctgggtag aactgcacttc agcaataatg |
| 356delA | atgtcgcag aacggagcgc ccgggatgca ggaggagagc ctgcagggct cctgggtag aactgcacttc agcaataatg |
| 235_236insA | atgtcgcag aacggagcgc ccgggatgca ggaggagagc ctgcagggct cctgggtag aactgcacttc agcaataatg |
| | |
| Wt BNIP3 | ggaacggg ggcagcgttcc agcctcggtttc tatttataatgga gacatggaa aaaatactg ctggacgcac agcatgagtc |
| 356delA | ggaacggg ggcagcgttcc agcctcggtttc tatttataatgga gacatggaa aaaatactg ctggacgcac agcatgagtc |
| 235_236insA | ggaacggg ggcagcgttcc agcctcggtttc tatttataatgga gacatggaa aaaatactg ctggacgcac agcatgagtc |
| | |
| Wt BNIP3 | tggacggag tagctccaaga gctctcactgtg acagcccacct cgctcgcag acaccacaa gataccaaca g ggcttct |
| 356delA | tggacggag tagctccaaga gctctcactgtg acagcccacct cgctcgcag acaccacaa gataccaaca g ggcttct |
| 235_236insA | tggacggag tagctccaaga gctctcactgtg acagcccacct cgctcgcag acaccacaa gataccaaca ga ggcttct |
| | |
| Wt BNIP3 | gaaacagat acccatagcatt ggagagaaa aacagctcacag tctgagga agatgatattg aaagaagga aagaagttg |
| 356delA | gaaacagat acccatagcatt ggagagaaa aacagctcacag tctgagga agatgatattg aaagaagga aagaagttg |
| 235_236insA | gaaacagat acccatagcatt ggagagaaa aacagctcacag tctgagga agatgatattg aaagaagga aagaagttg |
| | |
| Wt BNIP3 | aaagcatctt gaagaaaaact cagattggata tggg attggtcaa gtcggcc ggaaaatattc cccccaagg agttcctcttta |
| 356delA | aaagcatctt gaagaaaaact cagattggata tggg ttggtcaa gtcggcc ggaaaatattc cccccaagg agttcctcttta |
| 235_236insA | aaagcatctt gaagaaaaact cagattggata tggg attggtcaa gtcggcc ggaaaatattc cccccaagg agttcctcttta |
| | |
| Wt BNIP3 | aacacccga agcgcacggcc accctcagca tgaggaacacga gcgtcatg aagaaagg gggcatattctc tgcagaattt |
| 356delA | aacacccga agcgcacggcc accctcagca tgaggaacacga gcgtcatg aagaaagg gggcatattctc tgcagaattt |
| 235_236insA | aacacccga agcgcacggcc accctcagca tgaggaacacga gcgtcatg aagaaagg gggcatattctc tgcagaattt |
| | |
| Wt BNIP3 | ctgaaagtttt ccttccatctctgc tgctctctcattt gctggccatcgg attggggat ctatattgga aggcgtctgac aacctccacc |
| 356delA | ctgaaagtttt ccttccatctctgc tgctctctcattt gctggccatcgg attggggat ctatattgga aggcgtctgac aacctccacc |
| 235_236insA | ctgaaagtttt ccttccatctctgc tgctctctcattt gctggccatcgg attggggat ctatattgga aggcgtctgac aacctccacc |
| | |
| Wt BNIP3 | agcacctttttg atgaagaactgg agtctgacttg gttcgttagtggat tacttctgag cttgcaaca tagctcactga agagctgttag |
| 356delA | agcacctttttg atgaagaactgg agtctgacttg gttcgttagtggat tacttctgag cttgcaaca tagctcactga agagctgttag |
| 235_236insA | agcacctttttg atgaagaactgg agtctgacttg gttcgttagtggat tacttctgag cttgcaaca tagctcactga agagctgttag |
| | |
| Wt BNIP3 | atcctggggt ggccacgtcactt gtgtttatttgttc tgtaaatgctgcg ttcctaattta gtaaaataa aagaatagac acc |
| 356delA | atcctggggt ggccacgtcactt gtgtttatttgttc tgtaaatgctgcg ttcctaattta gtaaaataa aagaatagac acc |
| 235_236insA | atcctggggt ggccacgtcactt gtgtttatttgttc tgtaaatgctgcg ttcctaattta gtaaaataa aagaatagac acc |

Figure 6

| | |
|---|---|
| Wt BNIP3 | MSQNGAPGMQEESLQGSWVELHFSNNGNGGSVPASVSIYNGDMEKILLDAQHESG |
| RSSSK 356delA | MSQNGAPGMQEESLQGSWVELHFSNNGNGGSVPASVSIYNGDMEKILLDAQHESG |
| RSSSK 235_236insA | MSQNGAPGMQEESLQGSWVELHFSNNGNGGSVPASVSIYNGDMEKILLDAQHESG |
| RSSSK Wt BNIP3 | SSHCDSPPRSQTPQDTNRASETDTHSIGEKNSSQSEEDDIERRKEVESILKKNSDWIW |
| DWSS 356delA | SSHCDSPPRSQTPQDTNRASETDTHSIGEKNSSQSEEDDIERRKEVESILKKNSDWIW |
| VGQV 235_236insA | SSHCDSPPRSQTPQDTNRGF |
| Wt BNIP3 | RPENIPPKEFLFKHPKRTATLSMRNTSVMKKGGIFSAEFLKVFLPSLLLSHLLAIGLGI |
| YIGRRLT 356delA 235_236insA | GRKIFPPRSSSLNTRSARPPSA |
| Wt BNIP3 356delA 235_236insA | TSTSTF |

METHODS FOR DETECTING CANCER AND MONITORING CANCER PROGRESSION

FIELD OF THE INVENTION

The present invention relates to methods and kits for detecting and monitoring the progression of cancer.

BACKGROUND OF THE INVENTION

The Bcl-2 family is a group of anti-apoptotic and pro-apoptotic proteins that regulate cell death. This regulation is determined by these proteins forming homodimer or heterodimer complexes with other members of the Bcl-2 family. When anti-apoptotic members form heterodimers with pro-apoptotic members cell death is inhibited. However, when pro-apoptotic members form homo or heterodimers with each other, cell death is induced. These protein complexes form primarily on the mitochondria. The pro-apoptotic complexes lead to mitochondrial changes in membrane potential, production of reactive oxygen species (ROS) and release of proteins from the mitochondria. These events lead to induction of cell death.

The Bcl-2 Nineteen Kilodalton Interacting Protein 3 (BNIP3) is a pro-apoptotic Bcl-2 family member that induces cell death independent of caspase activation and release of mitochondrial cytochrome c (5,8). It does require changes in mitochondrial membrane potential ($\Delta\psi m$) and production of reactive oxygen species (ROS) to induce cell death (5,11). BNIP3 contains a PEST domain that targets BNIP3 for degradation, a putative BH3 domain conserved among Bcl-2 family members, a conserved domain (CD) conserved between C. elegans and humans, and a TM domain that targets BNIP3 to the mitochondria essential for BNIP3-induced cell death (12,15). Hypoxic regions within tumors express high levels of BNIP3 (7,10). However, it is unclear what function BNIP3 plays in hypoxic regions of tumors where tumor cells remain viable. Malignant gliomas are one of the most aggressive tumors in cancer with tumor hypoxia limiting responses to multimodality therapy, including radiation and chemotherapy (1,16).

SUMMARY OF THE INVENTION

The inventors have shown that mutant BNIP3 is a marker for solid tumors and tumor hypoxia, and that mutant BNIP3 is a prognostic indicator for tumors that are resistant to treatment with chemotherapy or radiation.

Accordingly, in one embodiment, the present invention provides a method of detecting cancer in a patient comprising:
   (a) testing a sample from the patient for the presence of mutant BNIP3, wherein the presence of mutant BNIP3 indicates that the patient has cancer.

In another embodiment, the present invention provides a method of monitoring the progression of cancer in a patient comprising:
   (a) testing a sample from the patient to determine the level of mutant BNIP3 in the sample; and
   (b) repeating step (a) at a later point in time and comparing the result of step (a) at an earlier point in time with the result of step (a) at a later point in time wherein a difference in the level of mutant BNIP3 is indicative of the progression of the cancer in the patient.

In a further embodiment, the present invention provides a method of identifying patients with cancer that is resistant to chemotherapy or radiation treatments comprising:

(a) testing a sample from a patient for the presence of mutant BNIP3, wherein the presence of mutant BNIP3 indicates that the patient has chemotherapy- or radiation-resistant cancer.

In preferred embodiments of the invention, the above methods are used to detect brain cancer.

In further preferred embodiments of the invention, the above methods are used to detect ovarian cancer.

In another embodiment, the present invention relates to an isolated nucleic acid sequence encoding a BNIP3 mutant, preferably a nucleic acid sequence encoding a proteins shown in SEQ ID NO:4 or SEQ ID NO:6, more preferably, a nucleic acid sequence shown in SEQ ID NO:3 or SEQ ID NO:5.

The invention also relates to isolated BNIP3 mutant proteins, preferably having a sequence shown in SEQ ID NO:4 or SEQ ID NO:6.

Other features and advantages of the present invention will become apparent from the (following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 5 shows an alignment of nucleotides representing the DNA sequence of wild type (SEQ ID NO:1) and two BNIP3 mutants (SEQ ID NOS:3 and 5). Boxes represent the sites of identified mutations in the DNA for BNIP3.

FIG. 6 shows predicted amino acids of wild type (SEQ ID NO:2) and two mutated BNIP3 proteins (SEQ ID NOS: 4 and 6). Bold amino acids represent different amino acids in mutant BNIP3 proteins compared to wild type.

DETAILED DESCRIPTION OF THE INVENTION

Figure 1:
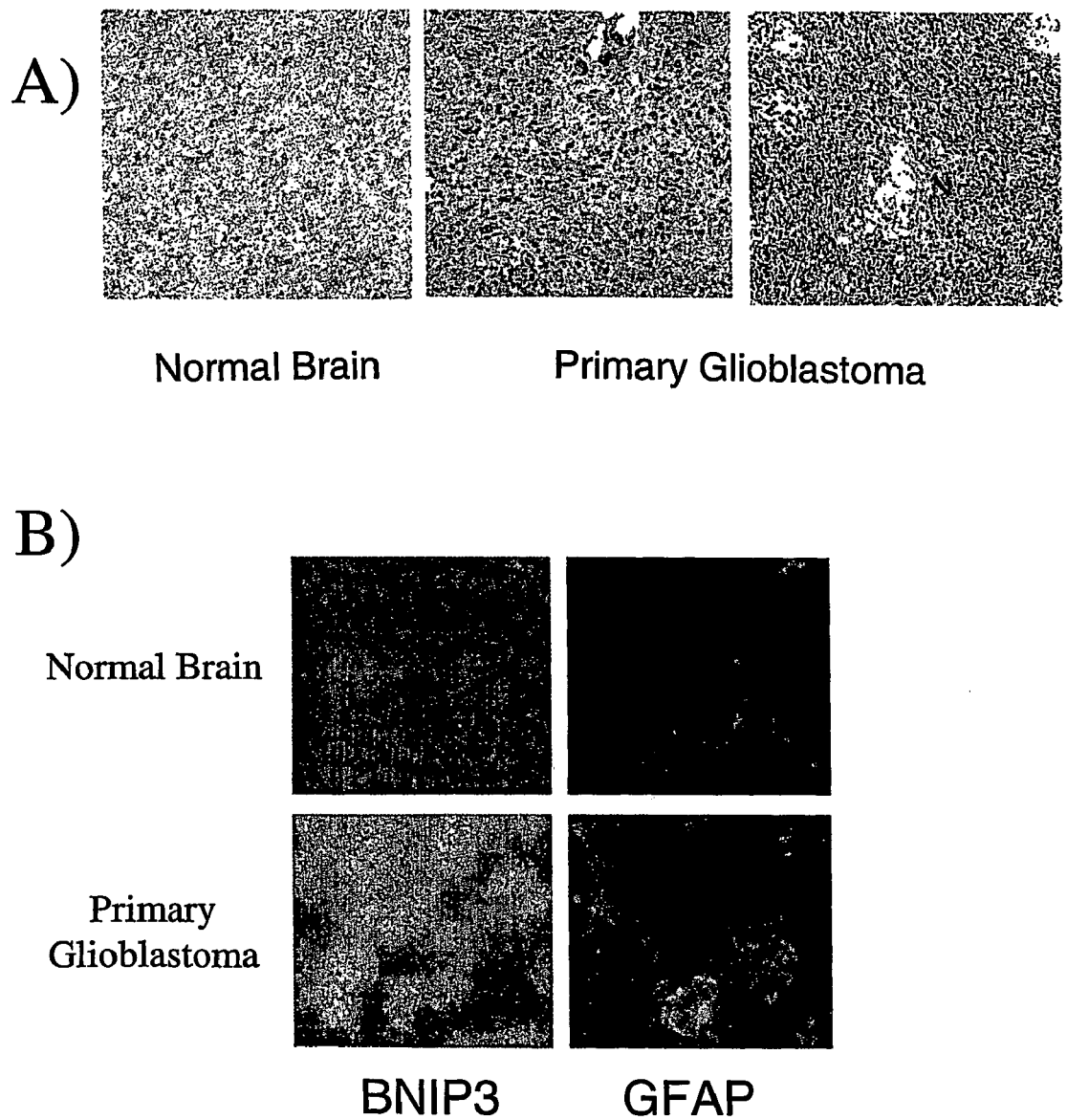
FIG. 1 shows that BNIP3 is highly expressed in brain tumors, especially hypoxic regions, but not in normal brain. A) Normal brain or primary glioblastoma multiforme (GBM) paraffin-embedded tumor tissue was immunostained by antibodies against BNIP3. A panel showing a GBM containing a necrotic region (N) was immunostained for BNIP3 (dark). B) Normal brain or primary GBM tissue was immunostained for BNIP3 and GFAP (marker for astrocytes). C) Normal brain and primary GBM sections were immunostained with antibodies against BNIP3 and HIF-1a. DNA was stained with Hoechst. D) Normal brain and primary GBM sections were immunostained with antibodies against BNIP3 and Glut-1 and analyzed on a confocal microscope. These results represent three independent experiments.
Figure 1:
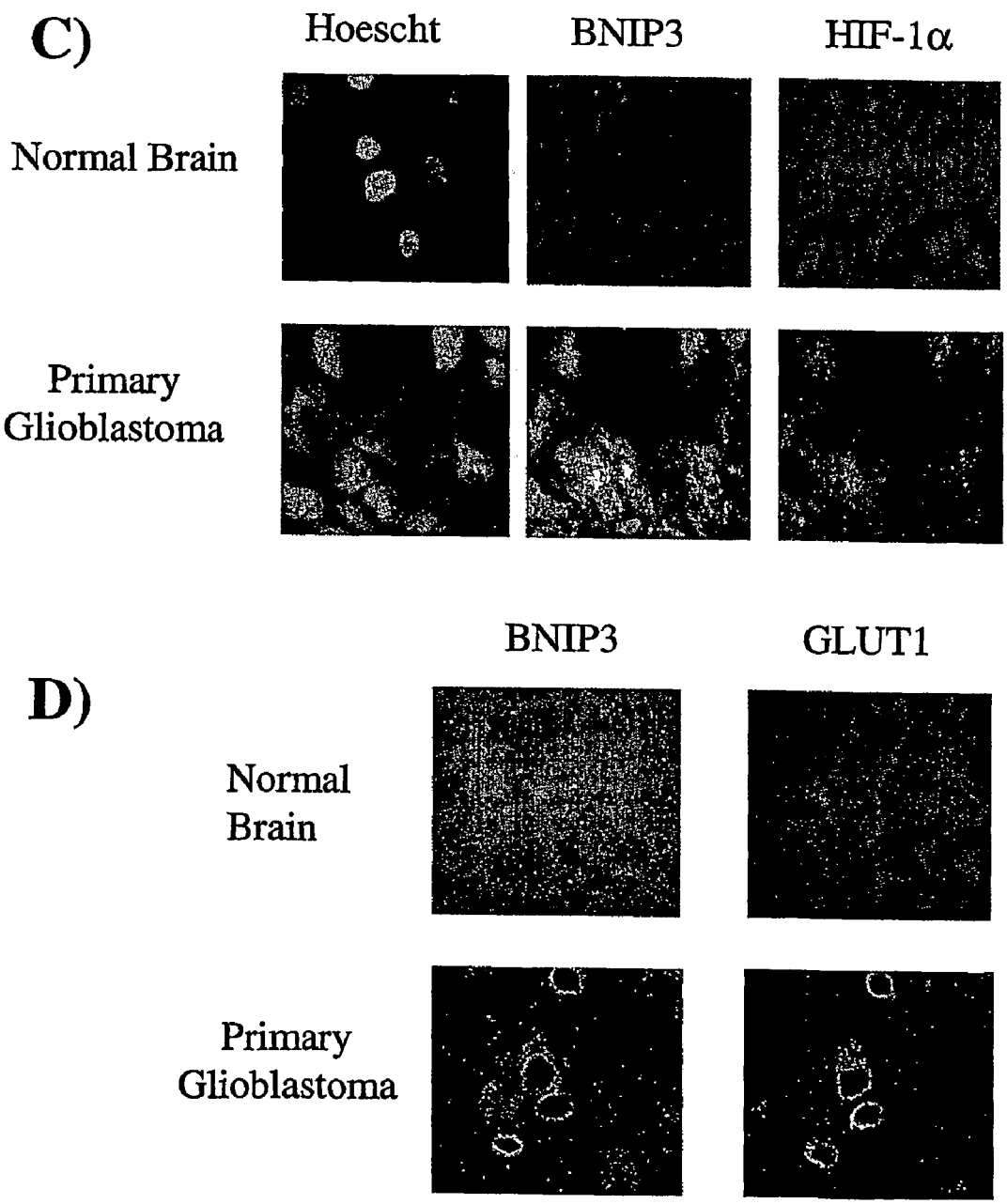

The present inventors have shown that mutant BNIP3 plays a functionally important role in the development of solid tumors and in resistance to chemotherapy and radiation treatments. Most solid tumors contain regions of low oxygen (hypoxia). The extent of hypoxic regions in tumors correlates with poor survival rates in patients suffering from cancer. This is primarily due to two reasons. First, hypoxic cells respond by increasing levels of proteins that protect cells from cell death induced by hypoxia. The second reason is that hypoxic cells are inherently resistant to radiation and chemotherapy. Radiation relies on the presence of oxygen to create free reactive oxygen species (ROS) to induce cell death. Under hypoxic condition, less ROS are produced and the tumor cells survive. Chemotherapy often requires delivery through the blood vessel network within the tumor. In hypoxic regions, these tumor blood vessels are absent or decreased blood flow was observed. This contributes significantly to the inability to deliver chemotherapeutic drugs to hypoxic cells or to the delivery of sub-lethal doses. Thus after treatment of solid tumors with chemotherapy and/or radiation, the hypoxic regions contain tumor cells that are the most likely to expand, repopulate the tumor and contribute to further resistance to cancer treatment. This is relevant in brain tumors, especially malignant astrocytomas, where there is no effective treatment and hypoxic regions are common. Understanding how hypoxic cells survive cell death under these physiologic conditions is essential to developing tumor biomarkers in order to select the best therapeutic options and to develop effective treatments.

The present inventors have found that the BNIP3 gene is mutated in brain tumors. The mutations introduce a frameshift in the conserved domain or the PEST domain of BNIP3, resulting in a truncated protein without a transmembrane (TM) domain. These mutations were detected both at the genomic DNA and mRNA levels. Deletion of the transmembrane domain prevents BNIP3 localization to the mitochondria and prevents induction of cell death. Furthermore, deletion of the transmembrane domain acts as a dominant negative protein preventing hypoxia induced cell death. BNIP3 is expressed in hypoxic regions of many tumors including breast and brain tumors but the cells remain viable. It is unclear how cells can survive with such high levels of a cell-death promoting protein. This paradox has, until now, been unexplained. The present inventors have found that the BNIP3 gene is mutated in approximately half of Grade IV astrocytomas (glioblastoma multiforme). In addition, other rare mutations have been discovered that introduce a stop codon leading to premature truncation of the protein. These mutations eliminate the ability of BNIP3 to induce cell death and might explain why BNIP3 expression is high in hypoxic regions of tumors. The inventors have further demonstrated that mutant BNIP3 localizes in the cytoplasm but fails to associate with the mitochondria, unlike wild-type BNIP3. In tumors with wild-type BNIP3, the protein is predominantly found in the nucleus. This localization to the nucleus prevents BNIP3's interaction with the mitochondria and hence failure to induce cell death. Since BNIP3 lacks a nuclear localization signal, it requires active transport from the cytoplasm into the nucleus through protein-protein interactions. It is conceivable that a nuclear transport protein over-expressed in tumors could re-localize or sequester wild-type BNIP3 in the nucleus preventing its induction of cell death. Alternatively, a negative regulator of BNIP3 nuclear transport could be altered in hypoxic cancer cells. Nevertheless, this phenomenon of nuclear sequestration or localization of BNIP3 has not been demonstrated before and could explain why wild-type BNIP3 is expressed at high levels in tumors.

BNIP3 localization to the nucleus likely represents a general mechanism whereby hypoxic cells avoid cell death and significantly contribute to tumorigenesis. In addition to the different localization patterns for wild-type (nuclear) and mutant (cytoplasmic) BNIP3 in tumors, BNIP3 expression can be used as a tumor biomarker/prognostic indicator for response to chemotherapy and/or radiation therapy. Diagnostic testing for (1) BNIP3 subcellular localization (nucleus or cytoplasm), and (2) BNIP3 mutation status provides essential information for the treatment of solid tumors in children and adults, including malignant brain tumors such as glioblastoma multiforme (GBM).

Accordingly, testing for the presence of mutant BNIP3 may be used in the prognostic and diagnostic evaluation of cancers involving mutant BNIP3, the identification of subjects with a predisposition to such cancers, in the monitoring of the progress of patients with mutant BNIP3 related cancers, and in identifying patients with cancer that is resistant to chemotherapeutic and radiation treatments.

In an embodiment of the invention, a method is provided for detecting cancer in a patient comprising:
(a) testing a sample from the patient for the presence of mutant BNIP3, wherein the presence of mutant BNIP3 indicates that the patient has cancer.

The term "mutant BNIP3" includes mutant versions of the Bcl-2 Nineteen Kilodalton Interacting Protein 3 gene or protein including, but not limited to, all of the known BNIP3 molecules, including those deposited in GenBank under accession number NM 004052 or those referred to in Chen, G. et al. 1999 *J. Biol. Chem.* 274: 7-10 (13) as well as any variants, analogs, derivatives or fragments thereof that are useful in detecting cancer. In a preferred embodiment the mutant BNIP3 comprises any mutation that results in elimination of the transmembrane domain in the BNIP3 protein, as well as any variants, analogs, derivatives or fragments thereof that are useful in detecting cancer. In a preferred embodiment, the mutant BNIP3 comprises a mutation in exon 3 of the BNIP3 gene as well as any variants, analogs, derivatives or fragments thereof that are useful in detecting cancer. In a further preferred embodiment, the mutant BNIP3 comprises any mutation in the PEST or CD domains, as well as any variants, analogs, derivatives or fragments thereof that are useful in detecting cancer. In another preferred embodiment, the mutant BNIP3 comprises a frame shift mutation in the PEST domain as a result of the insertion of adenosine (A) at nucleotide 236 (235_236insA) (SEQ ID NO: 5) that results in elimination of the transmembrane domain in the BNIP3 protein (SEQ ID NO:6), as well as any variants, analogs, derivatives or fragments thereof that are useful in detecting cancer. In another preferred embodiment, the mutant BNIP3 comprises a frame shift mutation in the CD domain as a result of the deletion of adenosine (A) at nucleotide 356 (356delA) (SEQ ID NO:3) that results in elimination of the transmembrane domain in the BNIP3 protein (SEQ ID NO:4), as well as any variants, analogs, derivatives or fragments thereof that are useful in detecting cancer.

The phrase "testing a sample for the presence of mutant BNIP3" includes testing for the presence of the mutant BNIP3 protein as well as testing for the presence of nucleic acid molecules encoding the mutant BNIP3 protein. Methods for detecting proteins and nucleic acids are discussed in greater detail below.

The term "cancer" as used herein includes all cancers that are associated with expression of mutant BNIP3. In a preferred embodiment, the cancer is brain cancer.

The term "sample from the patient" as used herein means any sample containing cancer cells that one wishes to detect including, but not limited to, biological fluids, tissue extracts, freshly harvested cells, and lysates of cells which have been incubated in cell cultures. In a preferred embodiment, the sample is brain tumor tissue.

The term "control sample" includes any sample that can be used to establish a base or normal level, and may include tissue samples taken from healthy persons or samples mimicking physiological fluid.

The method of the invention may be used in the diagnosis and staging of cancer, in particular brain cancer. The invention may also be used to monitor the progression of a cancer and to monitor whether a particular treatment is effective or not. In particular, the method can be used to confirm the absence or removal of all tumor tissue following surgery, cancer chemotherapy, and/or radiation therapy. The methods can further be used to monitor cancer chemotherapy and tumor reappearance, or to determine in advance whether chemotherapy and radiation treatments would be effective.

In an embodiment, the invention contemplates a method for monitoring the progression of cancer in a patient, comprising:

(a) testing a sample from the patient to determine the level of mutant BNIP3 in the sample; and (b) repeating step (a) at a later point in time and comparing the result of step (a) at an earlier point in time with the result of step (a) at a later point in time wherein a difference in the level of mutant BNIP3 is indicative of the progression of the cancer in the patient.

In particular, increased levels of mutant BNIP3 at the later time point may indicate that the cancer is progressing and that the treatment (if applicable) is not being effective. In contrast, decreased levels of mutant BNIP3 at the later time point may indicate that the cancer is regressing and that the treatment (if applicable) is effective.

The inventors have also found that mutant BNIP3 is a marker for the development of solid tumors and resistance to chemotherapy and radiation treatments. Accordingly, the present invention provides a method of identifying patients with cancer that is resistant to chemotherapy or radiation treatments comprising:

(a) testing a sample from a patient for the presence of mutant BNIP3, wherein the presence of mutant BNIP3 indicates that the patient has chemotherapy- or radiation-resistant cancer.

A variety of methods can be employed for the above described diagnostic and prognostic evaluation of cancers involving mutant BNIP3, and the identification of subjects with a predisposition to such disorders. Such methods may rely, for example, the detection of nucleic acid molecules encoding mutant BNIP3, and fragments thereof, or the detection of mutant BNIP3 protein using, for example, antibodies directed against mutant BNIP3, including peptide fragments. Each of these is described below.

(a) Methods for Detecting Nucleic Acid Molecules

In one embodiment, the methods of the invention involve the detection of nucleic acid molecules encoding mutant BNIP3. Those skilled in the art can construct nucleotide probes for use in the detection of nucleic acid sequences encoding mutant BNIP3 in samples. Suitable probes include nucleic acid molecules based on nucleic acid sequences encoding at least 5 sequential amino acids from regions of mutant BNIP3, preferably they comprise 15 to 30 nucleotides. Regions of mutant BNIP3 include the region surrounding nucleotide 356 or nucleotides 235/236 of the BNIP3 gene. In particular, a nucleotide probe may be designed to detect one of the BNIP3 mutants shown in FIG. 5 (SEQ ID NOS:3 and 5).

A nucleotide probe may be labeled with a detectable substance such as a radioactive label which provides for an adequate signal and has sufficient half-life such as $^{32}P$, $^{3}H$, $^{14}C$ or the like. Other detectable substances which may be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleotide to be detected and the amount of nucleotide available for hybridization. Labeled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect genes, preferably in human cells, that encode mutant BNIP3. The nucleotide probes may also be useful in the diagnosis of disorders involving a mutant BNIP3 in monitoring the progression of such disorders, or monitoring a therapeutic treatment. In an embodiment, the probes are used in the diagnosis of, and in monitoring the progression of cancer, preferably brain cancer.

The probe may be used in hybridization techniques to detect genes that encode mutant BNIP3 proteins. The technique generally involves contacting and incubating nucleic acids (e.g. recombinant DNA molecules, cloned genes) obtained from a sample from a patient or other cellular source with a probe under conditions favorable for the specific annealing of the probes to complementary sequences in the nucleic acids. After incubation, the non-annealed nucleic acids are removed, and the presence of nucleic acids that have hybridized to the probe if any are detected.

The detection of nucleic acid molecules may involve the amplification of specific gene sequences using an amplification method such as polymerase chain reaction (PCR), followed by the analysis of the amplified molecules using techniques known to those skilled in the art, such as but not limited to signal-strand conformation polymorphism (SSCP) and allelic specific PCR. Suitable primers can be routinely designed by one of skill in the art. Specifically one can conduct SSCP on exon 3 or the PEST domain of BNIP3 as described in Example 1. For SSCP analysis, genomic DNA can be extracted from tissue such as primary tumor tissue or blood samples. PCR primers can be designed, for example, primers flanking the intron/exon junction of exon 3 of the BNIP3 gene. Analysis of PCR products on a non-denaturing polyacrylamide gel can detect a single base pair insertion or deletion.

Hybridization and amplification techniques described herein may be used to assay qualitative and quantitative aspects of expression of genes encoding mutant BNIP3. For example, RNA may be isolated from a cell type or tissue known to express a gene encoding mutant BNIP3, and tested utilizing the hybridization (e.g. standard Northern analyses) or PCR techniques referred to herein. The techniques may be used to detect differences in transcript size which may be due to normal or abnormal alternative splicing. The techniques may be used to detect quantitative differences between levels of full length and/or alternatively splice transcripts detected in normal individuals relative to those individuals exhibiting symptoms of a cancer involving a mutant BNIP3 protein or gene.

The primers and probes may be used in the above-described methods in situ i.e. directly on tissue sections (fixed and/or frozen) of patient tissue obtained from biopsies or resections.

Accordingly, the present invention provides a method of detecting cancer in a patient comprising:

(a) extracting nucleic acid molecules comprising the mutant BNIP3 gene or portion thereof from a sample from the patient;

(b) amplifying the extracted nucleic acid molecules using the polymerase chain reaction;

(c) determining the presence of nucleic acid molecules encoding mutant BNIP3; and (d) comparing the level of mutant BNIP3 in the sample to a control sample, wherein the presence of increased levels of mutant BNIP3 as compared to the control indicates that the patient has cancer.

(b) Methods for Detecting Mutant BNIP3 Proteins

In another embodiment, the methods of the invention involve the detection of mutant BNIP3 proteins. In one embodiment, mutant BNIP3 proteins may be detected by sequencing the BNIP3 protein and determining if there is a difference in the amino acid sequence compared to the wild type BNIP3 as shown in FIG. 6 (or as is known in the art). In a preferred embodiment, one can detect one of the BNIP3 mutants shown in FIG. 6 and SEQ ID NOS:4 and 6.

In another embodiment, the mutant BNIP3 proteins may be detected by comparing the size of the protein with the wild type protein. As mentioned previously, the two mutant proteins shown in FIG. 6 (SEQ ID NOS: 4 and 6) lack the transmembrane domain of the protein and would therefore have a lower molecular weight than the wild type protein. Specifically, the 235_236insA mutant BNIP3 protein has a predicted size of approximately 12 kDa and the 356delA mutant BNIP3 protein has a predicted size of approximately 20 kDa, whereas the wild type protein has a predicted size of approximately 30 kDa. Size differences between proteins can be detected using a variety of biochemical techniques including rapid high-performance reversed phase liquid chromatographic methods, GC MS methods, hydrophobic chromatography (for example using a butyl-Toyopearl 650 column), successive chromatography on DEAE-cellulose, Bio-Gel P-60, and DEAE-Sephadex™ column, and/or gel electrophoresis (such as SDS-PAGE) and as such may be used to detect the mutant BNIP3 protein.

In yet another embodiment, mutant BNIP3 protein is detected using antibodies that specifically bind to mutant BNIP3 or antibodies that bind specifically to wild type BNIP3. Antibodies to both wild type and mutant BNIP3 proteins can readily be prepared by a person skilled in the art. As described in Example 1, the inventors have prepared antibodies to wild type BNIP3 that do not bind to the mutant BNIP3 proteins. In particular, antibodies that recognize both wild type BNIP3 and mutant BNIP3, and antibodies to wild type BNIP3 that do not bind to the mutant BNIP3 proteins, can be used advantageously. Performing an assay with a first antibody that recognizes both wild type and mutant NIP3 permits the determination of whether BNIP3, either wild type or mutant, is present. Performing a second assay against a sample from the same source, using a second antibody to wild type BNIP3 that does not bind to the mutant BNIP3 proteins, permits the determination of whether the BNIP3 present is wild type or mutant.

Antibodies to mutant BNIP3 protein may be prepared using techniques known in the art. For example, by using a peptide of mutant BNIP3 (such as the sequences shown in FIG. 6 or SEQ ID NOS:4 and 6), polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the protein or peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (22) as well as other techniques such as the human B-cell hybridoma technique (23), the EBV-hybridoma technique to produce human monoclonal antibodies (24), and screening of combinatorial antibody libraries (25). Hybridoma cells can be screened immunochemically for production of antibodies specifically reactive with the peptide and the monoclonal antibodies can be isolated.

The term "antibody" as used herein is intended to include fragments thereof which also specifically react with a mutant BNIP3 or fragments thereof. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes the gene product of mutant BNIP3 antigens of the invention (See, for example, Morrison et al., Proc. Natl. Acad. Sci. U.S.A. 81,6851 (1985); Takeda et al., Nature 314,452 (1985), Cabilly et al., U.S. Pat. No. 4,816, 567; Boss et al., U.S. Pat. No. 4,816,397; Tanaguchi et al., European Patent Publication EP171496; European Patent Publication 0173494, United Kingdom patent GB 2177096B). It is expected that chimeric antibodies would be less immunogenic in a human subject than the corresponding non-chimeric antibody.

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/ 06193 or EP 0239400). Humanized antibodies can also be commercially produced (Scotgen Limited, 2 Holly Road, Twickenham, Middlesex, Great Britain.)

Specific antibodies, or antibody fragments, such as, but not limited to, single-chain Fv monoclonal antibodies reactive against mutant BNIP3 may also be generated by screening expression libraries encoding immunoglobulin genes, or portions thereof, expressed in bacteria with peptides produced from the nucleic acid molecules of mutant BNIP3. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)). Alternatively, a SCID-hu mouse, for example the model developed by Genpharm, can be used to produce antibodies or fragments thereof.

Antibodies specifically reactive with mutant BNIP3, or derivatives, such as enzyme conjugates or labeled derivatives, may be used to detect mutant BNIP3 in various samples (e.g. biological materials). They may be used as diagnostic or prognostic reagents and they may be used to detect abnormalities in the level of protein expression, or abnormalities in the structure, and/or temporal, tissue, cellular, or subcellular location of a mutant BNIP3. In vitro immunoassays may also be used to assess or monitor the efficacy of particular therapies. The antibodies of the invention may also be used in vitro to determine the level of expression of a gene encoding mutant BNIP3 in cells genetically engineered to produce a mutant BNIP3 protein.

The antibodies may be used in any known immunoassays which rely on the binding interaction between an antigenic determinant of mutant BNIP3 and the antibodies. Examples of such assays are radioimmunoassays, enzyme immunoassays (e.g. ELISA), immunofluorescence, immunoprecipitation, latex agglutination, hemagglutination, and histochemical tests. The antibodies may be used to detect and quantify mutant BNIP3 in a sample in order to determine its role in cancer and to diagnose the cancer. In particular, the antibodies of the invention may be used in immunohistochemical analyses, for example, at the cellular and subcellular level, to detect a mutant BNIP3 protein, to localize it to particular cells and tissues, and to specific subcellular locations, and to quantitate the level of expression.

Cytochemical techniques known in the art for localizing antigens using light and electron microscopy may be used to detect mutant BNIP3. Generally, an antibody of the invention may be labeled with a detectable substance and a mutant BNIP3 protein may be localised in tissues and cells based upon the presence of the detectable substance. Examples of detectable substances include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualized by electron microscopy.

The antibody or sample may be immobilized on a carrier or solid support which is capable of immobilizing cells, antibodies etc. For example, the carrier or support may be nitrocellulose, or glass, polyacrylamides, gabbros, and magnetite. The support material may have any possible configuration including spherical (e.g. bead), cylindrical (e.g. inside surface of a test tube or well, or the external surface of a rod), or flat (e.g. sheet, test strip). Indirect methods may also be employed in which the primary antigen-antibody reaction is amplified by the introduction of a second antibody, having specificity for the antibody reactive against mutant BNIP3 protein. By way of example, if the antibody having specificity against mutant BNIP3 protein is a rabbit IgG antibody, the second antibody may be goat anti-rabbit gamma-globulin labeled with a detectable substance as described herein.

Where a radioactive label is used as a detectable substance, mutant BNIP3 may be localized by radioautography. The results of radioautography may be quantitated by determining the density of particles in the radioautographs by various optical methods, or by counting the grains.

Labeled antibodies against mutant BNIP3 protein may be used in locating tumor tissue in patients undergoing surgery i.e. in imaging. Typically for in vivo applications, antibodies are labeled with radioactive labels (e.g. iodine-123, iodine-125, iodine-131, gallium-67, technetium-99, and indium-111). Labeled antibody preparations may be administered to a patient intravenously in an appropriate carrier at a time several hours to four days before the tissue is imaged. During this period unbound fractions are cleared from the patient and the only remaining antibodies are those associated with tumor tissue. The presence of the isotope is detected using a suitable gamma camera. The labeled tissue can be correlated with known markers on the patient's body to pinpoint the location of the tumor for the surgeon.

Accordingly, in another embodiment the present invention provides a method for detecting cancer in a patient comprising:
 (a) contacting a sample from the patient with an antibody that binds to mutant BNIP3;
 (b) detecting the level of mutant BNIP3 in the sample; and
 (c) comparing the level of mutant BNIP3 in the sample to a control sample, wherein increased levels of mutant BNIP3 as compared to the control indicates that the patient has cancer.

II. Kits

The methods described herein may be performed by utilizing pre-packaged diagnostic kits comprising the necessary reagents to perform any of the methods of the invention. For example, the kits may include at least one specific nucleic acid or antibody described herein, which may be conveniently used, e.g., in clinical settings, to screen and diagnose patients and to screen and identify those individuals exhibiting a predisposition to developing cancer. The kits may also include nucleic acid primers for amplifying nucleic acids encoding mutant BNIP3 in the polymerase chain reaction. The kits can also include nucleotides, enzymes and buffers useful in the method of the invention as well as electrophoretic markers such as a 200 bp ladder. The kit will also include detailed instructions for carrying out the methods of the invention.

III. Isolated Mutants

The invention further relates to an isolated nucleic acid sequence encoding a BNIP3 mutant of the invention, preferably a nucleic acid sequence encoding a protein shown in SEQ ID NO:4 or SEQ ID NO:6, more preferably a nucleic acid sequence shown in SEQ ID NO:3 or SEQ ID NO:5.

The invention also includes isolated BNIP3 mutant proteins, preferably having a sequence shown in SEQ ID NO:4 or SEQ ID NO:6.

The following non-limiting examples are illustrative of the present invention:

EXAMPLES

Example 1

Malignant gliomas are the most commonly diagnosed brain tumor (1,2). Tumor hypoxia is a major limitation in treating these tumors with radiation and chemotherapy (3,4). The Bcl-2 Nineteen Kilodalton Interacting Protein 3 (BNIP3) is a hypoxia-inducible pro-apoptotic member of the Bcl-2 family transcriptionally activated by HIF-1α (5,7). BNIP3 binds to mitochondria through its transmembrane (TM) domain and induces cell death (5,8,9). Although BNIP3 is expressed at high levels in hypoxic regions of tumors, it paradoxically fails to induce cell death (7,10). In this example, the inventors have determined that BNIP3 is expressed at high levels in hypoxic regions of primary (or de novo) glioblastoma multiforme (GBM) tumors compared to normal brain. It has been discovered that BNIP3 is mutated in 33% of GBM tumors leading to a truncated protein with elimination of the TM domain. Tumor-derived mutant BNIP3 fails to induce cell death, localize with the mitochondria or induce loss of mitochondrial membrane potential ($\Delta\psi m$) in glioma cells. In addition to its loss of cell killing activity, mutant BNIP3 also inhibits hypoxia-induced cell death in glioma cells, in part by forming heterodimers with wild-type (wt) BNIP3. Moreover, the inventors have found elevated levels of wt BNIP3 in the nucleus of viable GBM tumor cells preventing BNIP3's association with mitochondria. Under normoxic conditions, BNIP3 expression is localized to the nucleus but during hypoxia, its cytoplasmic expression is increased with localization to mitochondria contributing to hypoxia-induced cell death. Taken together, loss of BNIP3 function in GBM tumors, either through mutations in BNIP3 rendering it unable to induce cell death or by retention of wt BNIP3 in the nucleus, suggests that BNIP3 acts as a tumor suppressor so that loss of BNIP3 function confers a survival advantage to GBM cells under hypoxic conditions.

Methods

RT-PCR and Cloning

RNA was isolated from frozen GBM tumors obtained from the Brain Tumor Tissue Bank (London, Canada) using RNA-Bee (Tel-Test) as per the manufacturer's instructions. Using oligonucleotide primers for the open reading frame of BNIP3 (forward primer atgtcgcagaacggagca (SEQ ID NO:7), and reverse primer tcaaaaggtgctggtggag (SEQ ID NO:8)), BNIP3 mRNA was amplified by polymerase chain reaction (PCR). One µg of RNA was used in the reaction. The PCR product was run on an agarose gel and the product isolated and sequenced at the sequencing facility at the Manitoba Institute of Cell Biology using the PCR primers. In addition, the PCR products for mutated BNIP3 cDNA were cloned into a TA vector (Invitrogen). The mutant BNIP3 cDNA was then subcloned into a pcDNA3 expression vector and used in subsequent transfection experiments.

Cell Culture and Transfections

Human glioblastoma cell lines U251 and U87 (obtained from Dr. V. W. Yong, University of Calgary and Dr. C. Hao, University of Alberta, respectively) were cultured in Dulbecco's modified essential medium (DMEM), supplemented with 10% fetal bovine serum, 2 mM L-glutamine, 1 mM MEM sodium pyruvate, 0.3% glucose and 100 units/ml penicillin/streptomycin. The cell lines were grown in a humidified incubator in the presence of 5% $CO_2$ at 37° C. Cells were maintained under hypoxic conditions (less than 1% oxygen) at 37° C. within a hypoxic chamber (Forma Scientific) filled with 5% $CO_2$ balanced with N2. Transfection experiments were carried out with the U87 and U251 cell lines. The cells were plated 48 hours prior to transfection to achieve approximately 40% confluence. The U87 cell line was transfected using Geneporter™ transfection reagent (GTS) and the U251 cell line using Effectene™ transfection reagent (Qiagen) as per the manufacturer's instructions.

Cell Death Curves

U251 and U87 cells were plated on 100 mm plates and grown to approximately 80% confluence, then incubated in hypoxic conditions for a time course of 0, 24, 48, 72 and 96 hours. Following incubation under hypoxia, the cells were trypsinized from the plates and centrifuged to collect a cell pellet. Cells were resuspended in 100 µl of media and 4 µl of acridine orange (100 µg/ml) and ethidium bromide (100 µg/ml) were added. A 10 µl aliquot was removed, placed on a microscope slide and a coverslip was applied. Using a fluorescein filter, the percentage of dead cells was determined by counting the number of DNA condensation nuclei. At least 200 cells were counted per sample as previously described (5).

β-Galactosidase Viability Assay

U87 and U251 cells were co-transfected in 100 mm culture plates with 2 µg of pcDNA3, pcDNA3-BNIP3, pcDNA3-BNIP3ΔTM, pcDNA3-356delA BNIP3 plasmid DNA and 0.5 µg of β-galactosidase reporter plasmid DNA. Transfected cells were incubated under normoxic conditions for 24 hours. Cells were fixed in 0.2% glutaraldehyde in 0.1 M PBS for 10 minutes and washed three times with 0.1 M PBS, then stained in X-gal buffer (0.5 mg/ml 5-bromo-4-chloro-3-indolyl-β-galactopyranoside, 3 mM $K_3Fe(CN)_6$, 3 mM $K_4Fe(CN)_6 \cdot 3H_2O$, 1 mM $MgCl_2$ in 0.1 M PBS) at 37° C. for 24 hours. The percentage of dead cells was calculated by assessing the number of rounded, condensed, blue-staining cells in the total population of flat, blue-staining cells. At least 200 cells were counted for each experiment.

Western Blotting

U251 cells were lysed for total protein or nuclear proteins as previously published (5). The lysates (60 mg) were separated by SDS-PAGE and transferred to nitrocellulose membranes. Membranes were blocked in 5% skim milk and western blotted with monoclonal antibodies against BNIP3 (1:1000) (5), pro-caspase 8 antibodies (1:1000, Upstate Biotech.), HDAC1 antibodies (1:1000, Upstate Biotech),) or β-actin (1:50, Sigma). The western blots were visualized with chemiluminescence (NEN-Dupont).

Immunostaininci and Confocal Microscony

Paraffin-embedded primary glioblastoma tumor section slides were obtained from the Brain Tumor Tissue Bank and baked in an oven (70° C.) for 20 minutes. The slides were deparaffinized, transferred to $H_2O$ for 5 minutes and placed in coplin jars with antigen retrieval solution (Dako Corporation) at 98.5° C. for 40 minutes. The slides were removed, cooled to room temperature (RT), and then washed three times for 5 minutes in PBS (0.5% Triton X100). Blocking solution (1×PBS, 0.2% Triton X100, 0.02% sodium azide, 5% goat serum and 0.1% bovine serum albumin) was added to each slide for 2 hours at RT. Primary antibodies (polyclonal anti-BNIP3 1:700 dilution (5), anti-GFAP 1:50 dilution (Dako), anti-HIF-1α 1:100 dilution (Novus), and anti-cytochrome c 1:100 dilution (gift from Dr. Andrews, McMaster University) were diluted in blocking solution and added to slides. The slides were incubated at 4° C. overnight and subsequently washed. The appropriate biotinylated secondary antibody (1:200 dilution, Vector Inc.) was prepared in blocking solution and added to the slides for 2 hours at RT then washed three times. Strepavidin conjugated to the appropriate fluorochrome (Texas Red or Oregon Green, Vector Inc.) in blocking solution (15mg/ml) was added to slides and incubated for 2 hours at RT in the dark. Vectashield™ mounting medium with DAPI stain (Vector) was added to each slide and a coverslip was placed and sealed. For double immunofluorescence, a second primary antibody was added and incubated overnight following the same procedure as the first primary antibody.

After transfection of U87 and U251 cell lines with 2 µg of pCDNA3, pCDNA3-BNIP3, pCDNA3-BNIP3ΔTM, or pCDNA3-356delA BNIP3, the cells were incubated for 24 and 48 hours, then trypsinized and centrifuged and then resuspended in 2 ml of media. A 200 µl aliquot was placed in a ThermoShandon cytospin at 1000 RPM for 5 minutes with medium-low acceleration. The slides obtained from the cytospin were immediately fixed with 3.7% formaldelyde in 1×PBS at RT for one hour. Following three washes with 1' PBS (0.1% NP40), slides were incubated with primary BNIP3 antibody (1:700 dilution in 10×FBS, 1×PBS, 0.1% NP40) for 1 hour at RT. The slides were then washed three times in PBS (0.1% NP40) and incubated with goat anti-rabbit fluorescein isothiocyanate (FITC)-conjugated secondary antibody (Sigma) for 1 hour. After three more washes, slides were mounted with coverslips containing Vectashield™ mounting medium mounting media with Hoescht dye (to counter-stain for nuclei). 200 or more cells were counted per sample to assess DNA condensation. Fluorescence was visualized and captured using an Olympus BX51 fluorescent microscope with a Photometrics Cool Snap CF camera and an Olympus IX70 inverted confocal laser microscope using Fluoview 2.0 software.

Determination of Mitochondrial Membrane Potential

U251 cells were grown in chamber slides and were co-transfected with pEGFP N1 (Clontech) and pCDNA3, pCDNA3-BNIP3, pCDNA3-BNIP3ΔTM, and pCDNA3-356delA BNIP3 using Geneporter™ transfection reagent (GTS) as per the manufacturer's instructions. After 16 h of incubation, the slides were washed twice with 1×Hepes-buffered saline solution (HBSS) and tetramethylrohdamine (TMRM; Molecular Probes) was added to the slides at 150 μm final concentration and incubated in the dark at RT for 10 min. The slides were then viewed on an Olympus IX70 inverted confocal laser microscope using Fluoview 2.0 software.

Immunohistochemical Staining of GBM Tumors

GBM slides were obtained from the Brain Tumor Tissue Bank. Upon deparaffinization and rehydration, the slides were then placed in a humidity chamber and 200 ml of blocking solution was placed on each slide and incubated for 2 hours at RT. Primary antibody was added to the slides (anti-BNIP3 1:200) and incubated at 4° C. overnight. The slides were then washed three times with 1×PBS (0.05% Triton X100). The secondary antibody (biotinylated goat anti-rabbit 1:200, Vector Inc.) was prepared in blocking solution and added to each slide. The slides were then incubated for 2 hours at RT, then washed and incubated in 0.3% $H_2O_2$ for 30 minutes at RT. The slides were then washed again Elite ABC solutions (Vector, Inc) were placed on the slides and incubated for 30 minutes at RT. After washing DAB substrate was added to the slides and incubated from 2-10 minutes until staining was detected. The reaction was stopped by the addition of water for 5 minutes. The slides were dehydrated through consecutive washes in graded ethanols (50-100%) and xylene and then mounted with Permount (Fisher). As a negative control, tissue samples were incubated with secondary antibodies alone. As a positive control, mouse skeletal muscle was stained for BNIP3 endogenously expressed at high levels in this tissue.

Single strand conformation polymorphism (SSCP)

Genomic DNA was extracted from primary GBM tumors or blood samples using DNeasy™ Tissue Kit per manufacture instructions (Qiagen). PCR primers flanking the intron/exon junction of exon 3 of the BNIP3 gene (accession number AL162274) were designed. The sequences of primers were cattcaccttccagcttacctgtg (SEQ ID NO:9) (forward) and cccattctattcacatcgccaag (SEQ ID NO:10) (reverse). PCR reaction mixtures contained 3ml of high fidelity Taq polymerase (Roche), 100 ng of DNA, 10 pmol of each primer, 0.4 ml of dNTP (5 mM dATP, 25 mM dCTP, 25 mM dGTP, 25 mM dTTP) mixtures and 0.5 ml of 10mci/ml a-$P^{32}$-dATP, 3 ml of 25mM $MgCL_2$, 5 ml of 10×PCR buffer in a total 50 ml volume. The labeled PCR products (5 ml) were mixed with 10 ml of formamide dye (95% formamide, 20mM EDTA, 0.05% xylene cyanol, 0.05% bromophenol blue) and denatured for 5 minutes at 95° C. Control samples were analyzed under denaturing and non-denaturing conditions. Each sample was applied on a non-denaturing 10% polyacrylamide gel.

Allele Specific PCR

Genomic DNA was extracted from primary GBM tumors. For allele specific PCR, a mutant-specific primer (gaccaatcccatatccaatctgag (SEQ ID NO:11)) was created with the 3'-terminal base complementary to the mutation in exon 4 of the BNIP3 gene (containing CD domain mutations). The second primer was common to both mutant and wildtype exon 4 of BNIP3 (ctgatgtgtcctctgtcaag (SEQ ID NO:12)). DNA (100 ng/ml) was added to the PCR reaction along with the primers. The annealing temperature for the PCR reaction was 59.8° C. and the PCR reaction was completed after 35 cycles. As a control, the mutant specific primer was replaced with a primer that recognizes both mutant and wildtype exon 4 sequence.

Antisense Experiments

Antisense oligonucleotide (5'-GCGCTCCGTTCTGCGA-CATG-3' (SEQ ID NO:13)) (Sigma Genesys, Oakville, ON) and sense oligonucleotide (5'-GTACAGCGTCTTGC-CTCGCG-3' (SEQ ID NO:14)) were complimentary to bases −1 to +19 of the human Bnip3 gene. Random sequence oligonucleotide (5'-GCAGTCAGCGACGTCGMGC-3' (SEQ ID NO:15)) contained the same bases in a scrambled sequence. Oligonucleotides were phosphorothioate-modified to prevent degradation. Oligonucleotides were diluted in Opti-MEM (Gibco BRL), mixed with oligofectamine (Invitrogen) and incubated with U87 cells for 4 hours then hypoxic media was added and cells were further incubated under hypoxia for 72 hours. Cell death was determined via acridine orange staining or cells were lysed and protein extracts were analyzed for BNIP3 expression as described above.

Results

In normal brain, BNIP3 is expressed at very low levels but in GBM tumors, the level of BNIP3 expression is significantly increased and its expression surrounds necrotic regions (a common surrogate marker for hypoxia, FIG. 1A). BNIP3 is also expressed in malignant astrocytes since GBM cells co-express BNIP3 and glial fibrillary acidic protein (GFAP), an intermediate filament marker for astrocytes. In normal glial cells, BNIP3 is expressed at very low levels (FIG. 1B). BNIP3, HIF-1α and Glut1 are often selectively expressed in hypoxic regions of tumors (7,10). In GBM tumors, HIF-1α and Glut1 are co-expressed with BNIP3 but they are not detected in normal brain (FIGS. 1C and 1D). This confirms that BNIP3 is expressed in hypoxic regions of GBM tumors.

Figure 2:
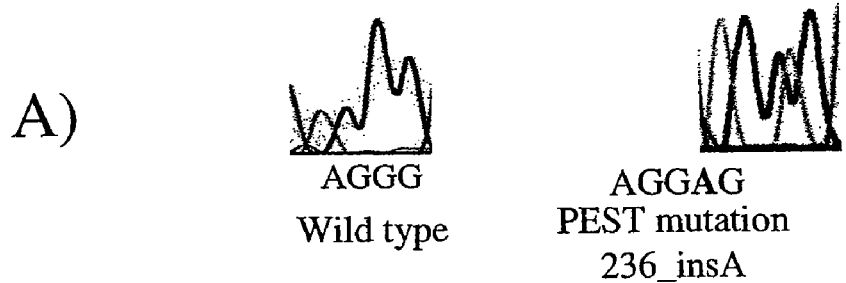
FIG. 2 shows that BNIP3 mutations are identified in genomic DNA obtained from malignant gliomas resulting in a truncated BNIP3 protein. A) Chromatograms of DNA sequences representing wild-type BNIP3 and mutations in the PEST domain from GBM tumors are presented. B) DNA was isolated from a primary GBM containing a mutation in the PEST domain and from normal brain (N). Single strand conformation polymorphism (SSCP) analysis was performed on exon 3 of BNIP3. The lower band represents wild-type BNIP3 while the upper band represents a one base pair insertion in the BNIP3 gene. Sequencing of this band confirmed the nucleotide insertion (data not shown). As a negative control, a non-denatured sample was also analyzed. DNA from a GBM tumor containing a mutation in the CD domain (GBM) and normal brain (N) was isolated. C) Blood samples were obtained from the Brain Tumor Tissue Bank and DNA was isolated. SSCP was performed. DNA from GBM tumors containing a PEST mutation was used as a positive control. As negative control for SSCP, a non-denatured sample was also analyzed. D) GBM tumors were also lysed and the isolated protein was Western blotted with i) a monoclonal antibody that recognizes only wild-type BNIP3. As a loading control, the blots were stripped and re-probed with an actin antibody. W represents wild-type BNIP3, whereas M represents mutant BNIP3. N represents normal brain. E) i) The ovarian cancer cell line SkOv3 and HEK293 cells (under normoxic (N) or hypoxic (H) conditions) were lysed and western blotted using polyclonal antibodies against BNIP3. Actin was used as a loading control. The specificity of the antibody was confirmed by incubating a fusion protein of the amino-terminal region of BNIP3 with the antibody. This effectively eliminated the reactive bands shown in this figure (data not shown). ii) SkOv3 and HEK293 cells were placed under hypoxic conditions for 72 hours, lysed and western blotted with a monoclonal antibody against BNIP3. iii) These cells were also immunostained with polyclonal antibodies against BNIP3 under normoxic and hypoxic conditions. DNA was stained with Hoechst dye.
Figure 2:
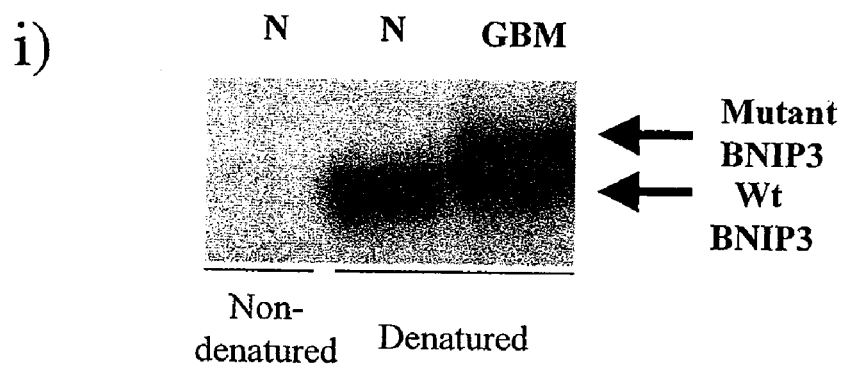
Figure 2:
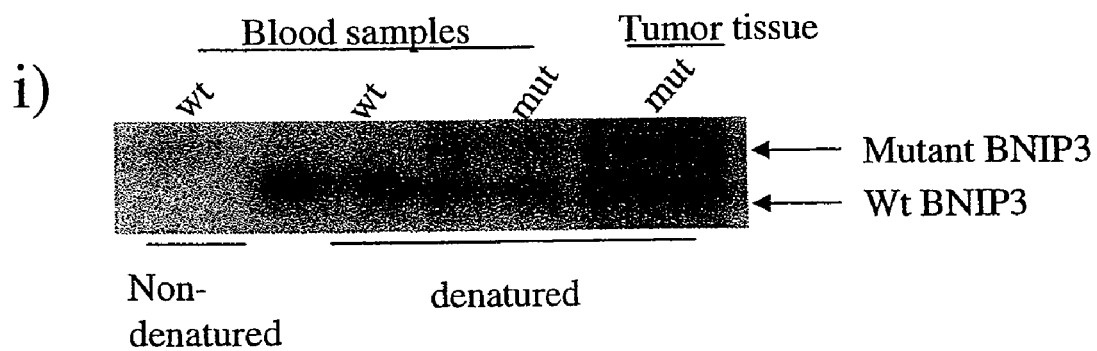
Figure 2:
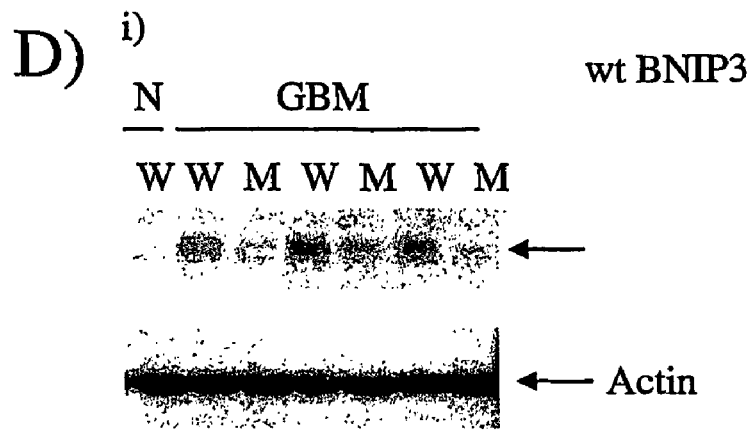
Figure 2:
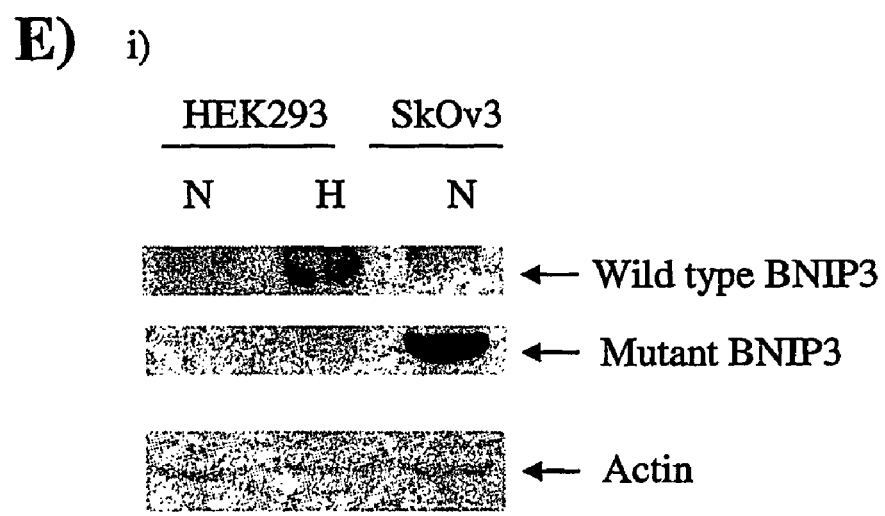
Figure 2:
Figure 2:
Figure 2:
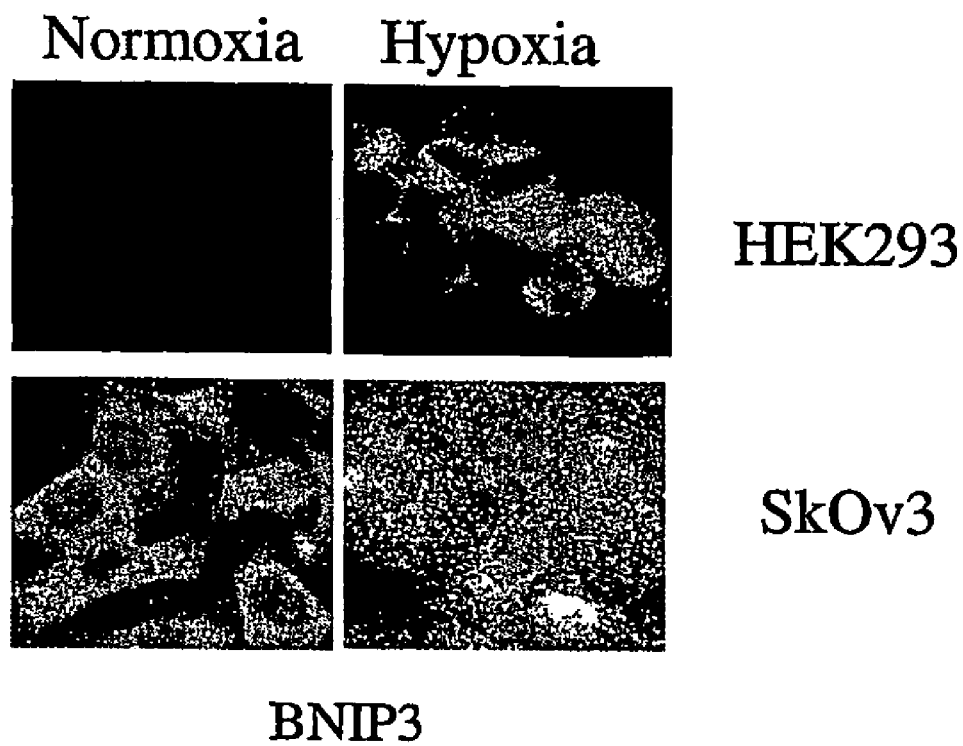

GBM tumors show increased BNIP3 expression but tumor cells remain viable. To determine whether wt BNIP3 cDNA is present in GBM tumors, the inventors sequenced the cDNA encoding BNIP3 from 24 tumors. 8 of 24 primary GBM tumors were found to demonstrate a mutation in the cDNA encoding the PEST or CD domains of BNIP3 (Table 1, FIG. 2A). These mutations all result in a frameshift eliminating the functional TM domain of BNIP3. In normal brain no mutations were found. To determine the presence of BNIP3 mutations in exon 3 (containing the PEST domain sequence), single strand conformation polymorphism (SSCP) analysis was performed. This showed an additional (upper) band in GBM DNA that was not present in DNA from normal brain (FIG. 2B i). Sequencing of the genomic tumor DNA and the additional band from SSCP confirmed the mutation (data not shown). These findings confirm that the BNIP3 gene is mutated in GBM tumors. To determine whether these mutations occur only in the tumor, blood samples from 7 of 8 patients with BNIP3 mutations were obtained. Three of these blood samples showed BNIP3 mutations. As a control, 9 of 16 patients with a wt BNIP3 gene in their tumor DNA had a blood sample available for analysis. All demonstrated a wt BNIP3 gene in their blood DNA (FIG. 2C, data not shown). These results suggest that BNIP3 mutations in non-tumor DNA might be germline.

All BNIP3 mutations that were detected in GBM tumors predict a truncated, non-functional protein. Western blots were performed with a monoclonal antibody that only recognizes wt BNIP3. In tumors where BNIP3 mutations were detected, the amount of wt BNIP3 was reduced (FIG. 2D). Using a polyclonal antibody that recognizes both wt and mutant BNIP3, a truncated band was found only in the tumors where BNIP3 was mutated (FIG. 2D). The inventors also investigated whether cancer cell lines contain mutations in BNIP3. In U87 and U251 cells as well as other glioma cell lines, BNIP3 was wild type but in the ovarian cancer cell line SkOv3, BNIP3 was mutated in the PEST domain (235_236insA). This mutation resulted in a truncated protein whereas wt BNIP3 was not detected in SkOv3 cells (FIG. 2E). Under normoxic conditions, mutant BNIP3 was expressed (FIG. 2E) correlating with constitutive HIF-1α expression (data not shown). Thus, the BNIP3 mutations that were identified result in a truncated protein.

Figure 3:
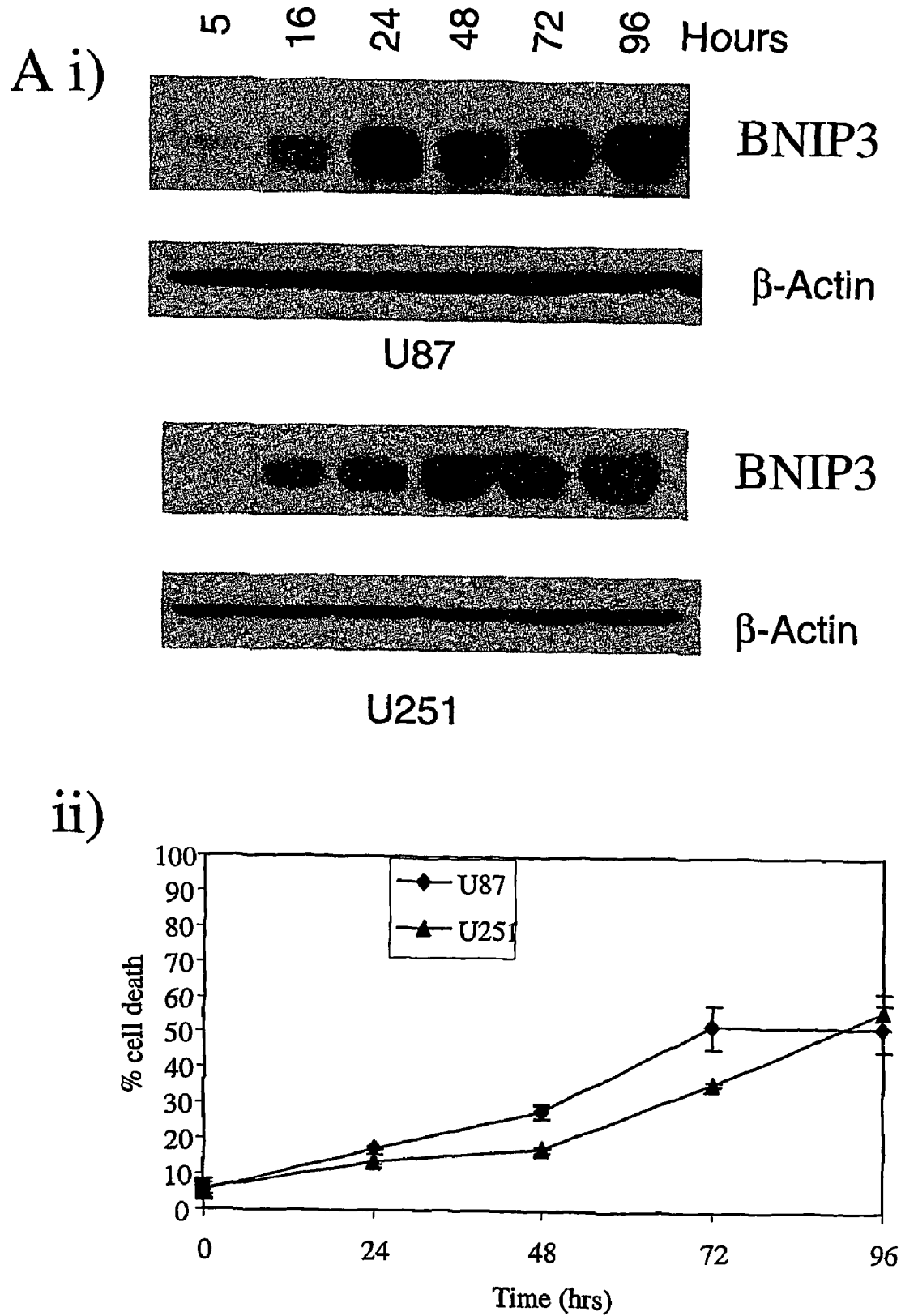
FIG. 3 shows that Mutant BNIP3 fails to induce cell death in glioblastoma cell lines. A) i) Glioma cell lines U87 and U251 were placed under hypoxic conditions and sampled at 24 hour intervals. Cells were lysed and western blotted for BNIP3 expression. Actin was used as a sample loading control. ii) U87 and U251 cells were also counted for cell death using acridine orange staining (detects DNA condensation) over a time course under hypoxic conditions. The error bars represent standard error from three separate and independent experiments. B) The glioblastoma cell lines U87 and U251 were transfected with wild-type (wt) BNIP3, transmembrane-deleted (DTM) BNIP3 and truncated BNIP3 (mutant CD domain, 356delA). The amount of cell death was determined by chromatin condensation as described in the Examples. These results were confirmed by morphological changes evident in cell death using a b-gal cell viability assay (data not shown). C) U251 cells were transfected with cDNA for BNIP3 DTM, truncated BNIP3 (mutant CD domain, 356delA) or empty vector (control) in combination with a b-gal expression vector. The cells were placed under hypoxic conditions for 72 hours and the amount of cell death was determined in cells expressing β-galactosidase. Normoxia represents the amount of cell death in U251 cells transfected with empty vector under normal oxidative conditions. Similar results were obtained for mutant BNIP3 with a mutated PEST domain, 255_256insA (data not shown). Error bars represent the standard error determined from three independent experiments. * denotes a p value <0.001 representing statistical significance between empty vector (control) transfected cells under hypoxia and cells transfected with BNIP3 DTM or truncated BNIP3 under hypoxia. D) U87 cells were transfected with antisense, sense, or scrambled oligonucleotides and placed under hypoxic conditions for 72 hours. The amount of cell death was determined. Controls cells were non-transfected (control) or those placed under normoxic conditions (normoxia). * represents a p value of <0.05 for statistical significance. A Western blot of BNIP3 under hypoxic conditions (72 hrs) is shown in the inserted box. E) U251 cells were transfected with cDNA for wt BNIP3 or truncated BNIP3 (mutant CD domain, 356delA) in an expression vector and placed under normoxic or hypoxic conditions. Forty-eight hours after transfection, the cells were stained with Mitotracker (mitochondrial stain) and with antibodies against BNIP3 (red). The cells were analyzed on a confocal microscope. These results represent three independent experiments. F) i) U251 cells were also transfected with cDNA for wt BNIP3, BNIP3 DTM, truncated BNIP3 (mutant CD domain, 356delA) or empty vector (control) in combination with an expression plasmid for green fluorescent protein (GFP). ii) The live cells were stained with TMRM and at least 200 cells were counted for the presence of TMRM staining. The percentage of cells that have lost TMRM staining (loss of membrane potential) was calculated. Error bars represent the standard error of three independent experiments. G) U87 cells were transfected with wild-type BNIP3 and truncated BNIP3 (mutant CD domain, 356delA) either alone or in combination. The cells were then lysed and western blotted i) with monoclonal antibodies against BNIP3 (recognizes only wild-type BNIP3) or ii) polyclonal antibodies (recognize both wild-type and truncated BNIP3) iii) His-tagged truncated BNIP3 was bound to nickel agarose beads and HEK293 cells transfected with vector alone or wt BNIP3 were lysed and added to these beads. The beads were washed with 250 mM imidazole and the resulting elution was Western blotted for wt BNIP3. As a negative control, beads alone were incubated with lysate expressing wt BNIP3. Lysate expressing wt BNIP3 was used as a positive control. The blots were stripped and reprobed with anti-His tag antibodies.
Figure 3:
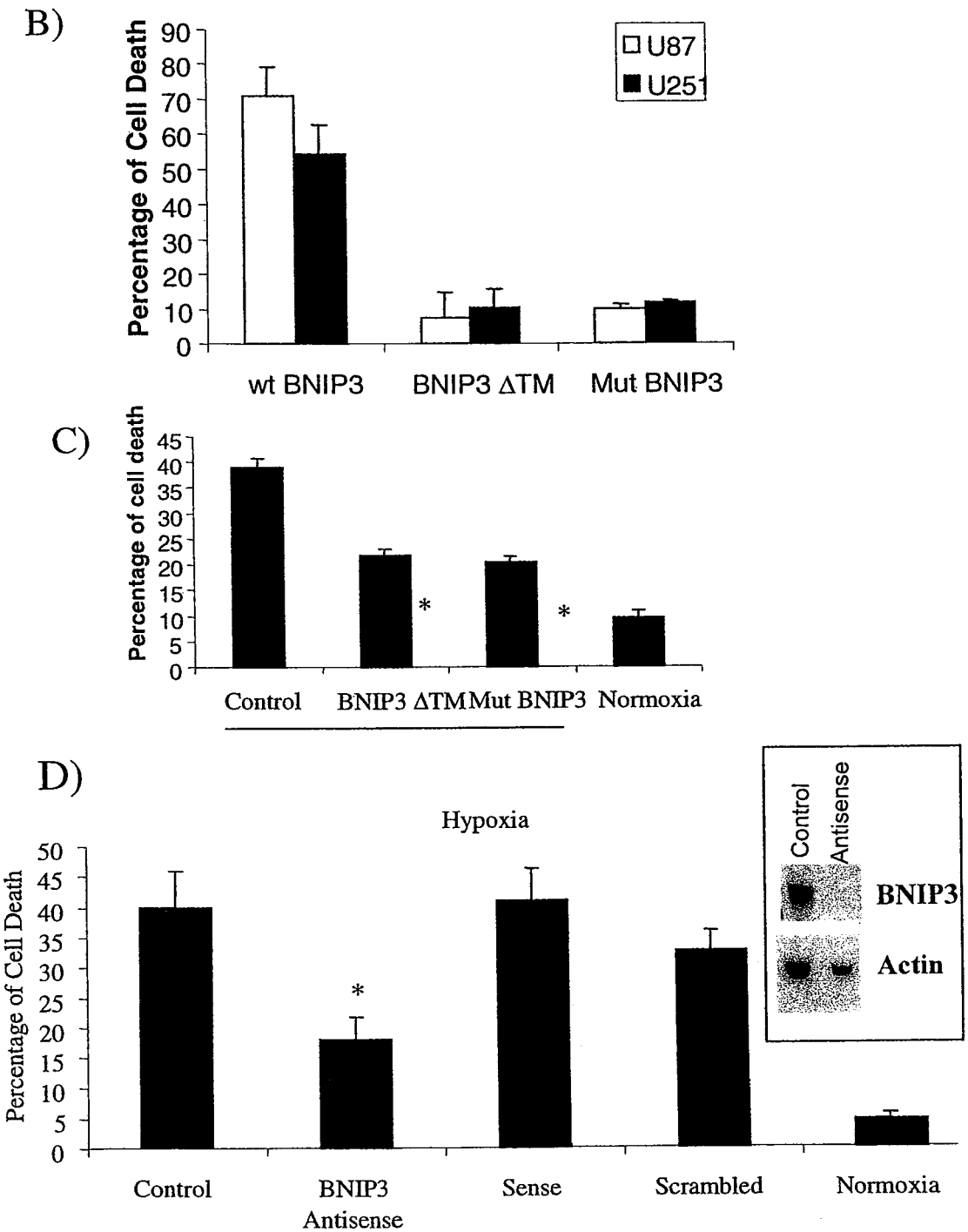
Figure 3:
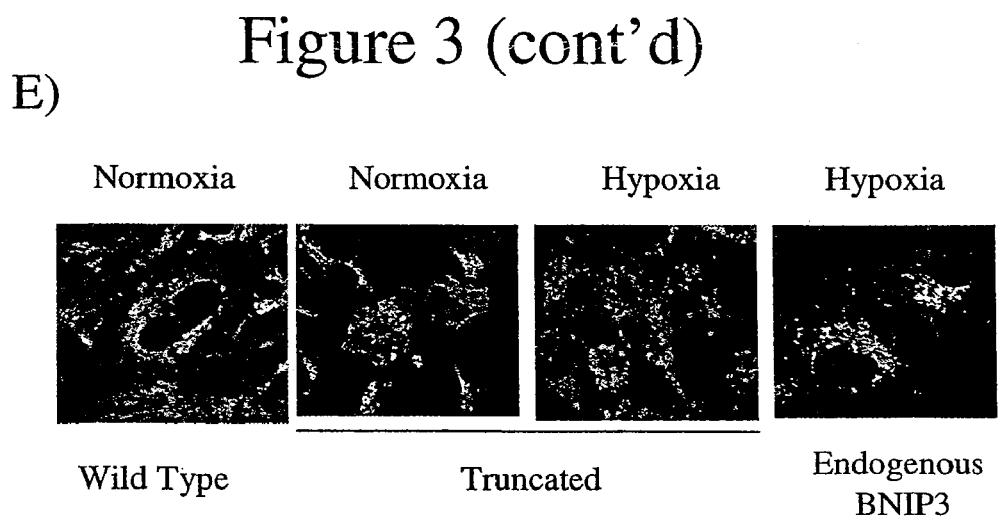
Figure 3:
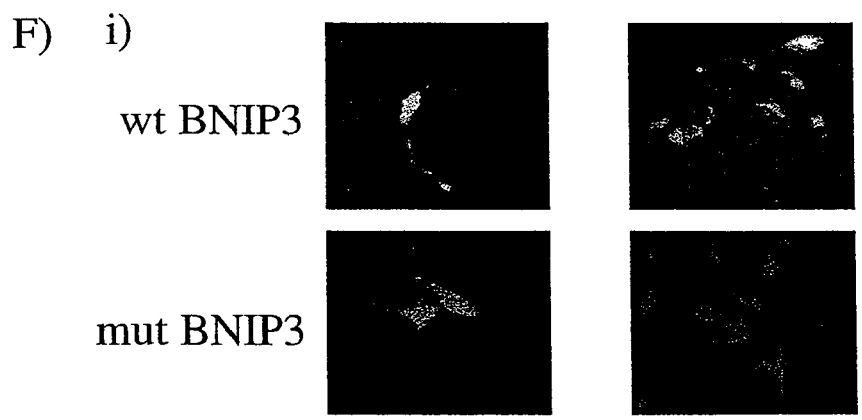
Figure 3:
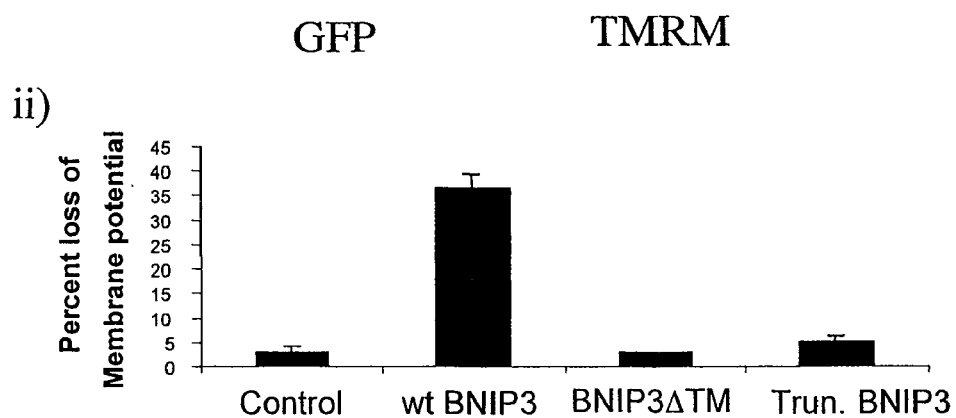
Figure 3:
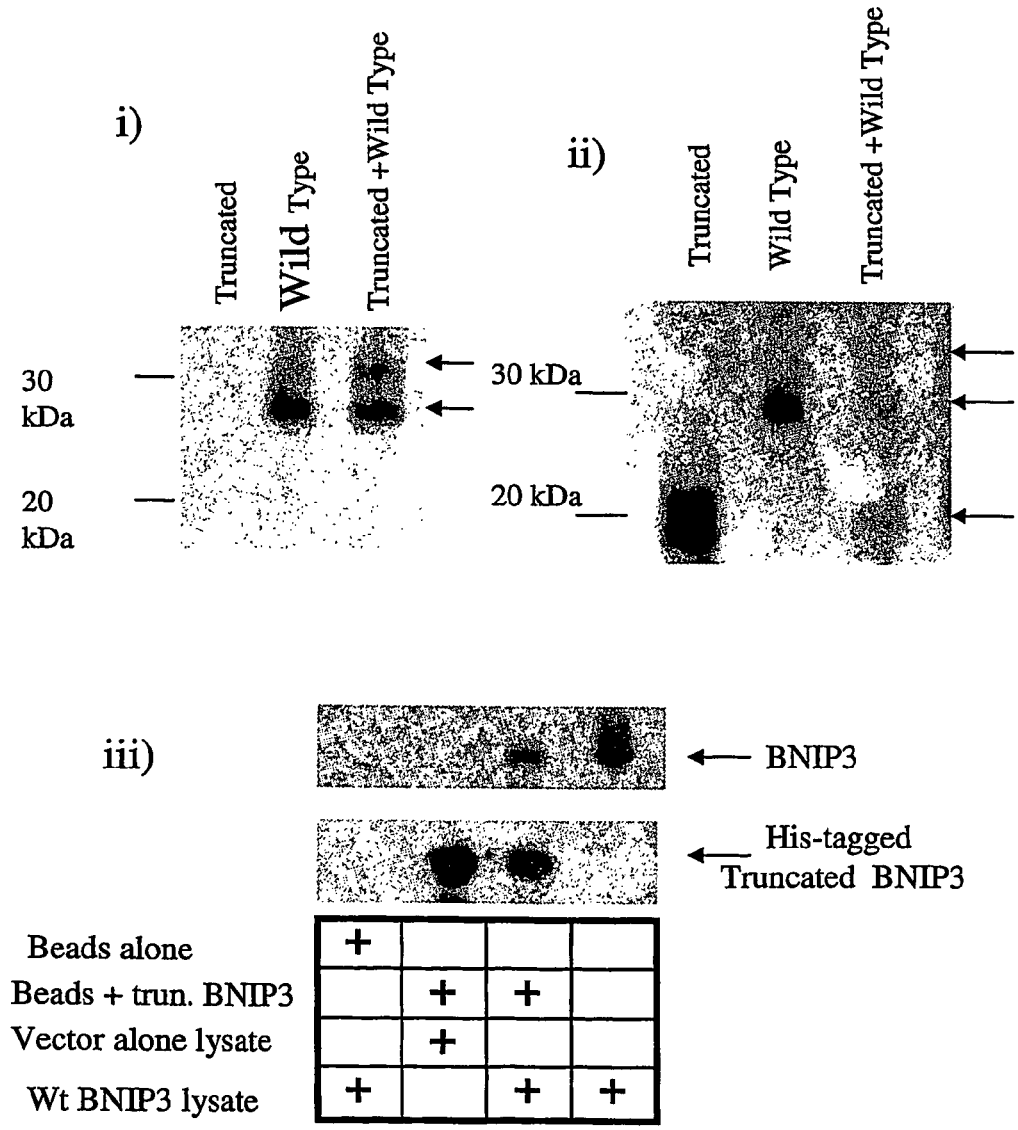

Since these BNIP3 mutations result in elimination of the TM domain, the inventors determined the ability of mutant BNIP3 to induce cell death in glioma cell lines. Under hypoxic conditions in U87 and U251 cells, BNIP3 protein is increased corresponding with cell death (FIG. 3A) suggesting that BNIP3 contributes to hypoxia-induced cell death (6). The cells were then transfected with wt BNIP3, TM deleted BNIP3 (BNIP3 ΔTM), 356delA BNIP3 (mutant CD domain, Mut BNIP3) or vector alone (control) resulting in only wt BNIP3 inducing cell death (FIG. 3B). Transfection of 235_236insA BNIP3 (mutant PEST domain) into glioma cells also failed to induce cell death (data not shown). BNIP3 ΔTM has been shown to act as dominant negative protein inhibiting hypoxia-induced cell death (6). U251 cells were transfected with BNIP3 ΔTM, 356delA BNIP3 (Mut BNIP3) or vector alone (control), and exposed to hypoxic conditions. While cells transfected with vector alone showed 40% cell death, cells transfected with BNIP3 ΔTM or 356delA BNIP3 showed 20% cell death, a 50% reduction, whereas cells under normoxia only had 10% cell death (FIG. 3C). To confirm that BNIP3 is necessary for hypoxia induced cell death in glioma cells, antisense oligonucleotides against BNIP3 (effectively blocks BNIP3 expression under hypoxia) inhibited hypoxia-induced cell death (FIG. 3D). This indicates that mutant (356delA) BNIP3 fails to induce cell death and acts in a dominant negative manner blocking wt BNIP3 mediated hypoxia-induced cell death. Thus, BNIP3 may act as a tumor suppressor in primary GBM tumors preventing the survival of glioma cells under hypoxic conditions.

BNIP3 induces cell death by associating with the outer membrane of mitochondria causing loss of Δψm (5,9,11,14, 17). To determine whether mutations in BNIP3 affect its mitochondrial localization, U251 cells were transfected with either wt BNIP3 or truncated (356delA) BNIP3. Only wt BNIP3 localized with mitochondria as indicated by dual fluorescence with a mitochondrial marker (FIG. 3E). Under hypoxic conditions, cells expressing 356delA BNIP3 also effectively blocked endogenous BNIP3 localization with mitochondria (FIG. 3E). In addition, U251 cells were transfected with wt BNIP3 or 356delA BNIP3 in combination with green fluorescent protein (GFP). Live cells were then stained with the membrane potential dye TMRM. In cells expressing wt BNIP3, TMRM staining decreased indicating loss of Δψm while cells expressing 356delA BNIP3 failed to change TMRM fluorescence (FIG. 3F). Since 356delA BNIP3 blocks wt BNIP3 localization to the mitochondria, wt BNIP3 and 356delA BNIP3 were transfected into U87 cells and Western blotted with antibodies that only recognize wt BNIP3. When both wt and mutant BNIP3 were co-expressed, a higher molecular weight protein band appeared. This was confirmed using an antibody that recognizes both wt and mutant BNIP3 (FIG. 3G). Using a His-tagged 356delA BNIP3 fusion protein bound to agarose beads, wt BNIP3 bound to this fusion protein indicating that wt and mutant BNIP3 form heterodimers (FIG. 3G). Thus, mutant (356delA) BNIP3 fails to localize to mitochondria and blocks wt BNIP3 mitochondrial localization likely mediated by heterodimerization of mutant and wt BNIP3. This supports a dominant negative mechanism underlying the inability of mutant BNIP3 to mediate hypoxia-induced cell death.

This discovery of BNIP3 mutations in one-third of primary GBM tumors approximates the mutation rate of the tumor suppressors p53 and PTEN in GBM tumors (16,18). As indicated by SSCP analysis (FIG. 2B), the wt BNIP3 allele is present along with the mutant BNIP3 allele in primary GBM tumors. This suggests that the mutations result in haploinsufficiency or a functional loss of heterozygosity (LOH) occurs in GBM tumor subpopulations, such as in hypoxic regions.

Figure 4:
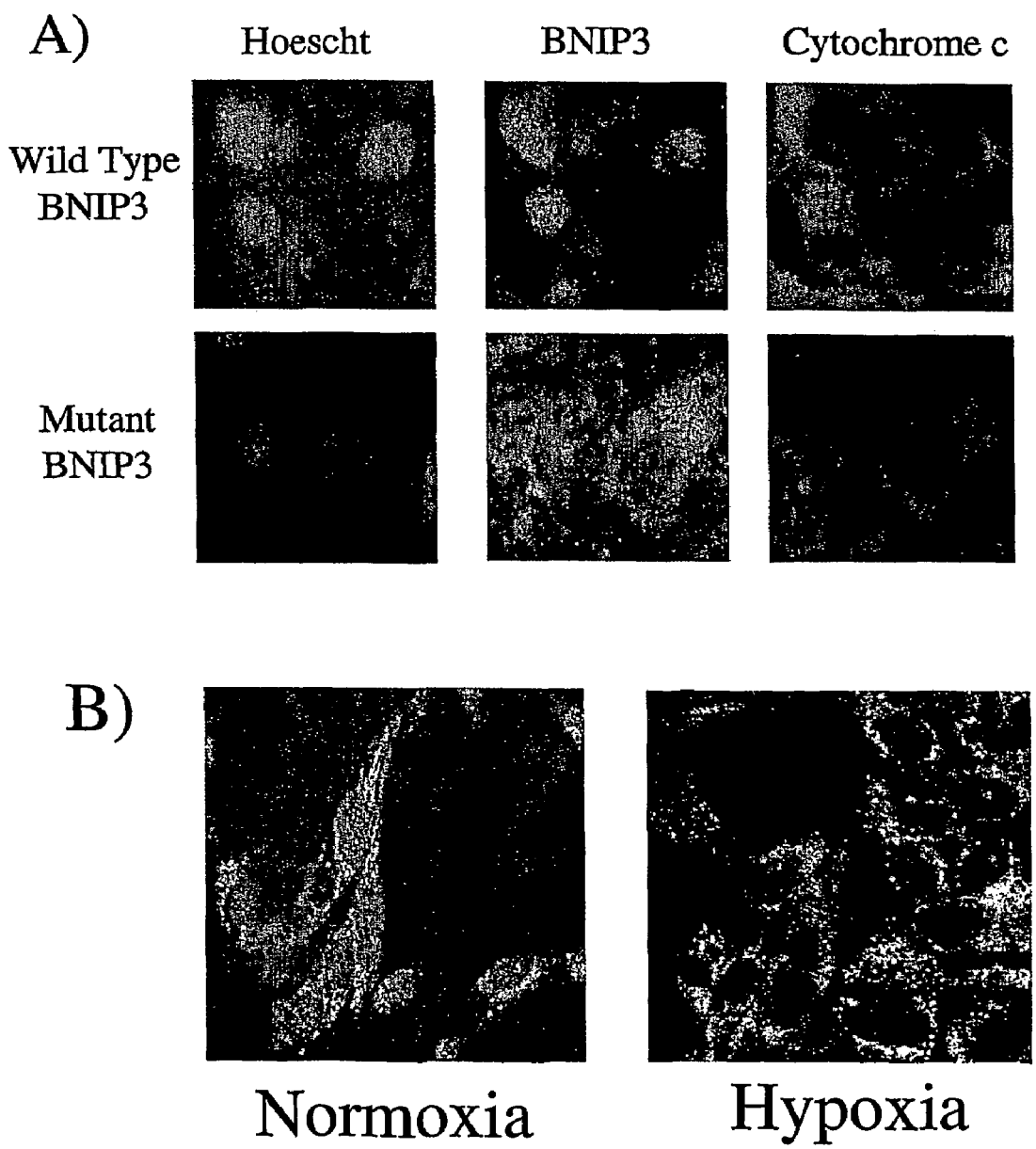
FIG. 4 shows that Wild-type BNIP3 localizes to the nucleus in primary glioblastoma tumors. A) Glioblastoma tumors with mutant BNIP3 (mutant PEST domain) or wild-type BNIP3 were stained with antibodies against BNIP3 and cytochrome c (marker for mitochondria). DNA was stained with Hoechst dye. The images were captured on a fluorescent microscope with deconvolution software (ImagePro Plus 4.5 and Sharpstack 4.5, MediaCybernetics). Similar results were obtained from other GBM tumors. In each panel, arrows represent staining of the same cell expressing mutant BNIP3 or wild-type BNIP3. B) U251 cells were placed under normoxic or hypoxic conditions and immunostained with antibodies against BNIP3, and with Mitotracker (green). Images were captured on a confocal laser microscope. Yellow staining represents co-localization of BNIP3 with Mitotracker staining. C) Cytoplasmic and nuclear fractions of U251 cells were isolated and lysed under normoxic and hypoxic conditions (48 hours). The lysate was Western blotted for BNIP3 expression and the blots were stripped and reprobed with antibodies against caspase 8 (cytoplasmic protein) and HDAC1 (nuclear protein) as controls.
Figure 4:
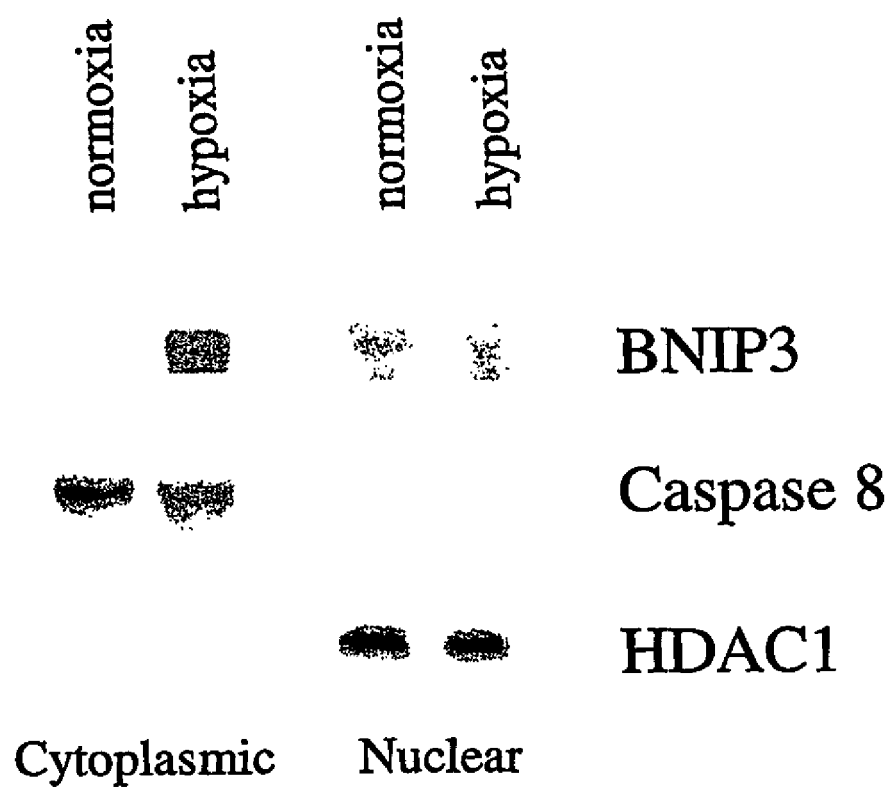

Since BNIP3 induces cell death by localizing to the mitochondria, the inventors investigated the subcellular localization of BNIP3 in GBM tumors. Tumors were labeled for BNIP3, cytochrome c (mitochondrial marker) and DNA. Tumors with wt BNIP3 predominantly showed nuclear localization and although low levels of cytoplasmic staining were detected, BNIP3 failed to localize with mitochondria. In contrast, tumors containing 356delA BNIP3 showed primarily a cytoplasmic localization, but similar to wt BNIP3, mutant BNIP3 was not localized to mitochondria (FIG. 4A). Indeed, 7 of 8 GBM tumors with BNIP3 mutations predominantly demonstrated cytoplasmic staining, whereas 19 of 20 GBM tumors with wt BNIP3 primarily showed nuclear staining. In U251 cells under normoxic conditions, endogenous BNIP3 was expressed at low levels in the nucleus (FIG. 4B). Under hypoxia, wt BNIP3 protein levels increased and were detected predominantly in the cytoplasm localized with mitochondria (FIG. 4B). Wt BNIP3 is present in nuclear fractions isolated from U251 cells but its expression in the nuclear compartment fails to increase during hypoxia, whereas in cytoplasmic fractions BNIP3 expression is dramatically increased (FIG. 4C). The retention of wt BNIP3 in the nucleus of GBM tumors provides an additional novel mechanism underlying how hypoxic cells within tumors avoid cell death.

HIF-1α transcriptionally activates target genes implicated in tumor survival (such as erythropoietin, vascular endothelial growth factor (VEGF) and the oncogene c-Met), or cell death, such as BNIP3 (4,6,7,19-21). The present results suggest that BNIP3-induced cell death is abrogated by mutations in BNIP3 or nuclear retention of wt BNIP3 tilting the balance in favor of tumor survival. Thus, loss of BNIP3 function represents a novel mechanism for glioma cells to avoid cell death under hypoxic conditions. The incidence and rate of BNIP3 mutations in other solid tumors remains to be determined. Nevertheless, BNIP3 mutations may represent a common mechanism for many types of cancer cells to survive under hypoxia.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

1. Gurney, J. G. & Kadan-Lottick, N. Brain and other central nervous system tumors: rates, trends, and epidemiology. *Curr Opin Oncol* 13, 160-6. (2001).
2. Kleihues, P. et al. The WHO classification of tumors of the nervous system. *J Neuropathol Exp Neurol* 61, 215-25; discussion 226-9. (2002).
3. Kayama, T., Yoshimoto, T., Fujimoto, S. & Sakurai, Y. Intratumoral oxygen pressure in malignant brain tumor. *J Neurosurg* 74, 55-9. (1991).
4. Sharp, F. R., Bergeron, M. & Bernaudin, M. Hypoxia-inducible factor in brain. *Adv Exp Med Biol* 502, 273-91. (2001).
5. Vande Velde, C. et al. BNIP3 and genetic control of necrosis-like cell death through the mitochondrial permeability transition pore. *Mol Cell Biol* 20, 5454-68. (2000).
6. Kothari, S. et al. BNIP3 plays a role in hypoxic cell death in human epithelial cells that is inhibited by growth factors EGF and IGF. *Oncogene* 22, 4734-44. (2003).
7. Guo, K. et al. Hypoxia induces the expression of the pro-apoptotic gene BNIP3. *Cell Death Differ* 8, 367-76. (2001).
8. Chen, G. et al. The E1B 19K/Bcl-2-binding protein Nip3 is a dimeric mitochondrial protein that activates apoptosis. *J Exp Med* 186, 1975-83. (1997).
9. Regula, K. M., Ens, K. & Kirshenbaum, L. A. Inducible expression of BNIP3 provokes mitochondrial defects and hypoxia-mediated cell death of ventricular myocytes. *Circ Res* 91, 226-31. (2002).
10. Sowter, H. M., Ratcliffe, P. J., Watson, P., Greenberg, A. H. & Harris, A. L. HIF-1-dependent regulation of hypoxic induction of the cell death factors BNIP3 and NIX in human tumors. *Cancer Res* 61, 6669-73. (2001).
11. Kim, J. Y., Cho, J. J., Ha, J. & Park, J. H. The carboxy terminal C-tail of BNip3 is crucial in induction of mitochondrial permeability transition in isolated mitochondria. *Arch Biochem Biophys* 398, 147-52. (2002).
12. Farooq, M. et al., Cloning of BNIP3h, a member of proapoptotic BNIP3 family genes. *Exp Mol Med* 33, 169-73. (2001).
13. Chen, G. et al., Nix and Nip3 form a subfamily of pro-apoptotic mitochondrial proteins. *J Biol Chem* 274, 7-10. (1999).
14. Yasuda, M., Han, J. W., Dionne, C. A., Boyd, J. M. & Chinnadurai, G. BNIP3alpha: a human homolog of mitochondrial proapoptotic protein BNIP. *Cancer Res* 59, 533-7. (1999).
15. Yasuda, M., Theodorakis, P., Subramanian, T. & Chinnadurai, G. Adenovirus E1B-19K/BCL-2 interacting protein BNIP3 contains a BH3 domain and a mitochondrial targeting sequence. *J Biol Chem* 273, 12415-21. (1998).
16. DeAngelis, L. Brain Tumors. *New England J. Medicine* 344, 114-123 (2001).
17. Ray, R. et al. BNIP3 heterodimerizes with Bcl-2/Bcl-X (L) and induces cell death independent of a Bcl-2 homology 3 (BH3) domain at both mitochondrial and nonmitochondrial sites. *J Biol Chem* 275, 1439-48. (2000).
18. Shapiro, J. R. Genetics of brain neoplasms. *Curr Neurol Neurosci Rep* 1, 217-24. (2001).
19. Semenza, G. L. HIF-1 and mechanisms of hypoxia sensing. *Curr Opin Cell Biol* 13, 167-71. (2001).
20. Pennacchietti, S. et al. Hypoxia promotes invasive growth by transcriptional activation of the met protooncogene. *Cancer Cell* 3, 347-61. (2003).
21. Forsythe, J. A. et al. Activation of vascular endothelial growth factor gene transcription by hypoxia-inducible factor 1. *Mol Cell Biol* 16, 4604-13. (1996).
22. Kohler and Milstein, *Nature* 256, 495-497 (1975).
23. Kozbor et al., *Immunol. Today* 4, 72 (1983).
24. Cole et al. *Monoclonal Antibodies in Cancer Therapy* (1985) Allen R. Bliss, Inc., pages 77-96.
25. Huse et al., *Science* 246, 1275 (1989).

TABLE 1

List of identified mutations found in cDNA encoding for BNIP3 in glioblastoma

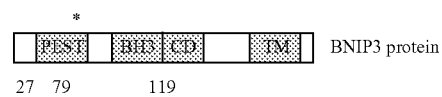 BNIP3 protein a.a.  27   79         119

| GBM tumor number | Mutation in cDNA | Location of the mutation in the protein | Functional Significance |
|---|---|---|---|
| 813 | Insertion A at nt 236 (235__236insA) | PEST domain | Elimination of the TM domain |
| 803 | Insertion A at nt236 (235__236insA) | PEST domain | Elimination of the TM domain |
| 819 | Insertion A at nt 236 (235__236insA) | PEST domain | Elimination of the TM domain |

* denotes the amino acid location of mutations found in BNIP3 cDNA.
PEST represents amino acids conserved in this domain,
BH3 represents Bcl-2 homology 3 domain,
CD represents conserved domain, and
TM represents transmembrane domain.

We claim:

1. A method of detecting cancer in a patient comprising:
   (a) testing a sample from the patient for the presence of a mutant Bcl-2 nineteen kilodalton interacting protein (BNIP3), comprising a deletion of adenosine at nucleotide 356 as shown in SEQ ID NO:3 (356delA) or an insertion of adenosine at nucleotide 235 (235 236insA) as shown in SEQ ID NO:5,
   (b) detecting the presence of said mutant BNIP3 indicates that the patient has cancer.

2. A method according to claim 1 wherein the sample is tissue or blood.

3. A method according to claim 1 wherein the cancer is brain cancer.

4. A method according to claim 1 wherein the cancer is ovarian cancer.

5. A method according to claim 1 wherein the sample is tested for the presence of nucleic acid molecules encoding mutant BNIP3 in step (a).

6. A method according to claim 5 wherein the sample is tested for the presence of mutant BNIP3 mRNA.

7. A method according to claim 1 wherein the presence of mutant BNIP3 protein is determined in step (a).

8. A method according to claim 7 wherein the mutant BNIP3 protein has the sequence shown in SEQ ID NO:4.

9. A method according to claim 7 wherein the mutant BNIP3 protein has the sequence shown in SEQ ID NO:6.

10. A method according to claim 7 wherein an antibody is used to determine the levels of the mutant BNIP3 protein.

11. A method of identifying patients with cancer that is resistant to chemotherapy or radiation treatments comprising:
    (a) testing a sample from a patient for the presence of mutant BNIP3 comprising a deletion of adenosine at nucleotide 356 as shown in SEQ ID NO:3 (356delA) or an insertion of adenosine at nucleotide 235 (235 236insA) as shown in SEQ ID NO:5,
    (b) detecting the presence of said mutant BNIP3 indicates that the patient has chemotherapy- or radiation- resistant cancer.

12. A method according to claim 11 wherein the sample is tissue or blood.

13. A method according to claim 11 wherein the cancer is brain cancer.

14. A method according to claim 11 wherein the cancer is ovarian cancer.

15. A method according to claim 11 wherein the sample is tested for the presence of nucleic acid molecules encoding mutant BNIP3 in step (a).

16. A method according to claim 15 wherein the sample is tested for the presence of mutant BNIP3 mRNA.

17. A method according to claim 11 wherein the sample is tested for the presence of mutant BNIP3 protein in step (a).

18. A method according to claim 17 wherein an antibody is used to detect the presence of mutant BNIP3 protein.

* * * * *

SEQUENCE LISTING

<160> NUMBER OF SEQ ID NOS: 15

<210> SEQ ID NO 1
<211> LENGTH: 745
<212> TYPE: DNA
<213> ORGANISM: Homo sapiens

```
<220> FEATURE:
<221> NAME/KEY: CDS
<222> LOCATION: (1)..(582)

<400> SEQUENCE: 1 atg tcg cag aac gga gcg ccc ggg atg cag gag gag agc ctg cag ggc      48
Met Ser Gln Asn Gly Ala Pro Gly Met Gln Glu Glu Ser Leu Gln Gly
 1               5                  10                  15 tcc tgg gta gaa ctg cac ttc agc aat aat ggg aac ggg ggc agc gtt      96
Ser Trp Val Glu Leu His Phe Ser Asn Asn Gly Asn Gly Gly Ser Val
             20                  25                  30 cca gcc tcg gtt tct att tat aat gga gac atg gaa aaa ata ctg ctg     144
Pro Ala Ser Val Ser Ile Tyr Asn Gly Asp Met Glu Lys Ile Leu Leu
         35                  40                  45 gac gca cag cat gag tct gga cgg agt agc tcc aag agc tct cac tgt     192
Asp Ala Gln His Glu Ser Gly Arg Ser Ser Ser Lys Ser Ser His Cys
 50                  55                  60 gac agc cca cct cgc tcg cag aca cca caa gat acc aac agg gct tct     240
Asp Ser Pro Pro Arg Ser Gln Thr Pro Gln Asp Thr Asn Arg Ala Ser
 65                  70                  75                  80 gaa aca gat acc cat agc att gga gag aaa aac agc tca cag tct gag     288
Glu Thr Asp Thr His Ser Ile Gly Glu Lys Asn Ser Ser Gln Ser Glu
                 85                  90                  95 gaa gat gat att gaa aga agg aaa gaa gtt gaa agc atc ttg aag aaa     336
Glu Asp Asp Ile Glu Arg Arg Lys Glu Val Glu Ser Ile Leu Lys Lys
            100                 105                 110 aac tca gat tgg ata tgg gat tgg tca agt cgg ccg gaa aat att ccc     384
Asn Ser Asp Trp Ile Trp Asp Trp Ser Ser Arg Pro Glu Asn Ile Pro
        115                 120                 125 ccc aag gag ttc ctc ttt aaa cac ccg aag cgc acg gcc acc ctc agc     432
Pro Lys Glu Phe Leu Phe Lys His Pro Lys Arg Thr Ala Thr Leu Ser
    130                 135                 140 atg agg aac acg agc gtc atg aag aaa ggg ggc ata ttc tct gca gaa     480
Met Arg Asn Thr Ser Val Met Lys Lys Gly Gly Ile Phe Ser Ala Glu
145                 150                 155                 160 ttt ctg aaa gtt ttc ctt cca tct ctg ctg ctc tct cat ttg ctg gcc     528
Phe Leu Lys Val Phe Leu Pro Ser Leu Leu Leu Ser His Leu Leu Ala
                165                 170                 175 atc gga ttg ggg atc tat att gga agg cgt ctg aca acc tcc acc agc     576
Ile Gly Leu Gly Ile Tyr Ile Gly Arg Arg Leu Thr Thr Ser Thr Ser
            180                 185                 190 acc ttt tgatgaagaa ctggagtctg acttggttcg ttagtggatt acttctgagc     632
Thr Phe ttgcaacata gctcactgaa gagctgttag atcctggggt ggccacgtca cttgtgttta     692
tttgttctgt aaatgctgcg ttcctaattt agtaaaataa agaatagac acc             745

<210> SEQ ID NO 2
<211> LENGTH: 194
<212> TYPE: PRT
<213> ORGANISM: Homo sapiens

<400> SEQUENCE: 2

Met Ser Gln Asn Gly Ala Pro Gly Met Gln Glu Glu Ser Leu Gln Gly
 1               5                  10                  15

Ser Trp Val Glu Leu His Phe Ser Asn Asn Gly Asn Gly Gly Ser Val
             20                  25                  30

Pro Ala Ser Val Ser Ile Tyr Asn Gly Asp Met Glu Lys Ile Leu Leu
         35                  40                  45

Asp Ala Gln His Glu Ser Gly Arg Ser Ser Ser Lys Ser Ser His Cys
```

```
                50                  55                  60
Asp Ser Pro Pro Arg Ser Gln Thr Pro Gln Asp Thr Asn Arg Ala Ser
 65                  70                  75                  80

Glu Thr Asp Thr His Ser Ile Gly Glu Lys Asn Ser Ser Gln Ser Glu
                 85                  90                  95

Glu Asp Asp Ile Glu Arg Arg Lys Glu Val Glu Ser Ile Leu Lys Lys
            100                 105                 110

Asn Ser Asp Trp Ile Trp Asp Trp Ser Ser Arg Pro Glu Asn Ile Pro
            115                 120                 125

Pro Lys Glu Phe Leu Phe Lys His Pro Lys Arg Thr Ala Thr Leu Ser
130                 135                 140

Met Arg Asn Thr Ser Val Met Lys Lys Gly Gly Ile Phe Ser Ala Glu
145                 150                 155                 160

Phe Leu Lys Val Phe Leu Pro Ser Leu Leu Leu Ser His Leu Leu Ala
                165                 170                 175

Ile Gly Leu Gly Ile Tyr Ile Gly Arg Arg Leu Thr Thr Ser Thr Ser
            180                 185                 190

Thr Phe

<210> SEQ ID NO 3
<211> LENGTH: 744
<212> TYPE: DNA
<213> ORGANISM: Homo sapiens
<220> FEATURE:
<221> NAME/KEY: CDS
<222> LOCATION: (1)..(432)

<400> SEQUENCE: 3
```

| atg tcg cag aac gga gcg ccc ggg atg cag gag gag agc ctg cag ggc | 48 |
|---|---|
| Met Ser Gln Asn Gly Ala Pro Gly Met Gln Glu Glu Ser Leu Gln Gly | |
|  1               5                  10                  15     | |

| tcc tgg gta gaa ctg cac ttc agc aat aat ggg aac ggg ggc agc gtt | 96 |
|---|---|
| Ser Trp Val Glu Leu His Phe Ser Asn Asn Gly Asn Gly Gly Ser Val | |
|             20                  25                  30         | |

| cca gcc tcg gtt tct att tat aat gga gac atg gaa aaa ata ctg ctg | 144 |
|---|---|
| Pro Ala Ser Val Ser Ile Tyr Asn Gly Asp Met Glu Lys Ile Leu Leu | |
|         35                  40                  45             | |

| gac gca cag cat gag tct gga cgg agt agc tcc aag agc tct cac tgt | 192 |
|---|---|
| Asp Ala Gln His Glu Ser Gly Arg Ser Ser Ser Lys Ser Ser His Cys | |
|     50                  55                  60                 | |

| gac agc cca cct cgc tcg cag aca cca caa gat acc aac agg gct tct | 240 |
|---|---|
| Asp Ser Pro Pro Arg Ser Gln Thr Pro Gln Asp Thr Asn Arg Ala Ser | |
| 65                  70                  75                  80 | |

| gaa aca gat acc cat agc att gga gag aaa aac agc tca cag tct gag | 288 |
|---|---|
| Glu Thr Asp Thr His Ser Ile Gly Glu Lys Asn Ser Ser Gln Ser Glu | |
|                 85                  90                  95     | |

| gaa gat gat att gaa aga agg aaa gaa gtt gaa agc atc ttg aag aaa | 336 |
|---|---|
| Glu Asp Asp Ile Glu Arg Arg Lys Glu Val Glu Ser Ile Leu Lys Lys | |
|            100                 105                 110         | |

| aac tca gat tgg ata tgg gtt ggt caa gtc ggc cgg aaa ata ttc ccc | 384 |
|---|---|
| Asn Ser Asp Trp Ile Trp Val Gly Gln Val Gly Arg Lys Ile Phe Pro | |
|            115                 120                 125         | |

| cca agg agt tcc tct tta aac acc cga agc gca cgg cca ccc tca gca | 432 |
|---|---|
| Pro Arg Ser Ser Ser Leu Asn Thr Arg Ser Ala Arg Pro Pro Ser Ala | |
| 130                 135                 140                    | |

```
tgaggaacac gagcgtcatg aagaaagggg gcatattctc tgcagaattt ctgaaagttt      492
tccttccatc tctgctgctc tctcatttgc tggccatcgg attggggatc tatattggaa      552
```

-continued

```
ggcgtctgac aacctccacc agcacctttt gatgaagaac tggagtctga cttggttcgt        612
tagtggatta cttctgagct tgcaacatag ctcactgaag agctgttaga tcctggggtg        672
gccacgtcac ttgtgtttat ttgttctgta aatgctgcgt tcctaattta gtaaaataaa        732
agaatagaca cc                                                            744
```

<210> SEQ ID NO 4
<211> LENGTH: 144
<212> TYPE: PRT
<213> ORGANISM: Homo sapiens

<400> SEQUENCE: 4

```
Met Ser Gln Asn Gly Ala Pro Gly Met Gln Glu Glu Ser Leu Gln Gly
1               5                  10                  15

Ser Trp Val Glu Leu His Phe Ser Asn Asn Gly Asn Gly Gly Ser Val
            20                  25                  30

Pro Ala Ser Val Ser Ile Tyr Asn Gly Asp Met Glu Lys Ile Leu Leu
        35                  40                  45

Asp Ala Gln His Glu Ser Gly Arg Ser Ser Ser Lys Ser Ser His Cys
    50                  55                  60

Asp Ser Pro Pro Arg Ser Gln Thr Pro Gln Asp Thr Asn Arg Ala Ser
65                  70                  75                  80

Glu Thr Asp Thr His Ser Ile Gly Glu Lys Asn Ser Ser Gln Ser Glu
                85                  90                  95

Glu Asp Asp Ile Glu Arg Arg Lys Glu Val Glu Ser Ile Leu Lys Lys
            100                 105                 110

Asn Ser Asp Trp Ile Trp Val Gly Gln Val Gly Arg Lys Ile Phe Pro
        115                 120                 125

Pro Arg Ser Ser Ser Leu Asn Thr Arg Ser Ala Arg Pro Pro Ser Ala
    130                 135                 140
```

<210> SEQ ID NO 5
<211> LENGTH: 746
<212> TYPE: DNA
<213> ORGANISM: Homo sapiens
<220> FEATURE:
<221> NAME/KEY: CDS
<222> LOCATION: (1)..(240)

<400> SEQUENCE: 5

```
atg tcg cag aac gga gcg ccc ggg atg cag gag gag agc ctg cag ggc        48
Met Ser Gln Asn Gly Ala Pro Gly Met Gln Glu Glu Ser Leu Gln Gly
1               5                  10                  15 tcc tgg gta gaa ctg cac ttc agc aat aat ggg aac ggg ggc agc gtt        96
Ser Trp Val Glu Leu His Phe Ser Asn Asn Gly Asn Gly Gly Ser Val
            20                  25                  30 cca gcc tcg gtt tct att tat aat gga gac atg gaa aaa ata ctg ctg        144
Pro Ala Ser Val Ser Ile Tyr Asn Gly Asp Met Glu Lys Ile Leu Leu
        35                  40                  45 gac gca cag cat gag tct gga cgg agt agc tcc aag agc tct cac tgt        192
Asp Ala Gln His Glu Ser Gly Arg Ser Ser Ser Lys Ser Ser His Cys
    50                  55                  60 gac agc cca cct cgc tcg cag aca cca caa gat acc aac aga ggc ttc        240
Asp Ser Pro Pro Arg Ser Gln Thr Pro Gln Asp Thr Asn Arg Gly Phe
65                  70                  75                  80 tgaaacagat acccatagca ttggagagaa aaacagctca cagtctgagg aagatgatat     300
tgaaagaagg aaagaagttg aaagcatctt gaagaaaaac tcagattgga tatgggattg     360
gtcaagtcgg ccggaaaata ttccccccaa ggagttcctc tttaaacacc cgaagcgcac     420
```

```
ggccaccctc agcatgagga acacgagcgt catgaagaaa gggggcatat tctctgcaga    480
atttctgaaa gttttccttc catctctgct gctctctcat ttgctggcca tcggattggg    540
gatctatatt ggaaggcgtc tgacaacctc caccagcacc ttttgatgaa gaactggagt    600
ctgacttggt tcgttagtgg attacttctg agcttgcaac atagctcact gaagagctgt    660
tagatcctgg ggtggccacg tcacttgtgt ttatttgttc tgtaaatgct gcgttcctaa    720
tttagtaaaa taaagaata gacacc                                          746

<210> SEQ ID NO 6
<211> LENGTH: 80
<212> TYPE: PRT
<213> ORGANISM: Homo sapiens

<400> SEQUENCE: 6

Met Ser Gln Asn Gly Ala Pro Gly Met Gln Glu Glu Ser Leu Gln Gly
1               5                   10                  15

Ser Trp Val Glu Leu His Phe Ser Asn Asn Gly Asn Gly Gly Ser Val
            20                  25                  30

Pro Ala Ser Val Ser Ile Tyr Asn Gly Asp Met Glu Lys Ile Leu Leu
        35                  40                  45

Asp Ala Gln His Glu Ser Gly Arg Ser Ser Ser Lys Ser Ser His Cys
    50                  55                  60

Asp Ser Pro Pro Arg Ser Gln Thr Pro Gln Asp Thr Asn Arg Gly Phe
65                  70                  75                  80

<210> SEQ ID NO 7
<211> LENGTH: 18
<212> TYPE: DNA
<213> ORGANISM: Artificial Sequence
<220> FEATURE:
<223> OTHER INFORMATION: Forward primer

<400> SEQUENCE: 7
atgtcgcaga acggagca                                                   18

<210> SEQ ID NO 8
<211> LENGTH: 19
<212> TYPE: DNA
<213> ORGANISM: Artificial Sequence
<220> FEATURE:
<223> OTHER INFORMATION: Reverse primer

<400> SEQUENCE: 8
tcaaaaggtg ctggtggag                                                  19

<210> SEQ ID NO 9
<211> LENGTH: 24
<212> TYPE: DNA
<213> ORGANISM: Artificial Sequence
<220> FEATURE:
<223> OTHER INFORMATION: Forward primer

<400> SEQUENCE: 9
cattcacctt ccagcttacc tgtg                                            24

<210> SEQ ID NO 10
<211> LENGTH: 23
<212> TYPE: DNA
<213> ORGANISM: Artificial Sequence
<220> FEATURE:
<223> OTHER INFORMATION: Reverse primer
```

```
<400> SEQUENCE: 10
cccattctat tcacatcgcc aag                                           23

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
gaccaatccc atatccaatc tgag              24

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ctgatgtgtc ctctgtcaag                                               20

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13
gcgctccgtt ctgcgacatg                                               20

<210> SEQ ID NO 14
<211> LENGTH: 20
<212> TYPE: DNA
<213> ORGANISM: Artificial Sequence
<220> FEATURE:
<223> OTHER INFORMATION: Sense Oligonucleotide

<400> SEQUENCE: 14
gtacagcgtc ttgcctcgcg                                               20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide

<400> SEQUENCE: 15
gcagtcagcg acgtcgaagc                                               20
```